(12) United States Patent
Ohashi et al.

(10) Patent No.: US 8,613,893 B2
(45) Date of Patent: Dec. 24, 2013

(54) SEALING MEMBER, CAP FOR REAGENT CONTAINER, AND REAGENT CONTAINER

(75) Inventors: Naoki Ohashi, Shizuoka (JP); Kiyoaki Kobayashi, Fuji (JP); Tetsuya Abe, Iwata (JP)

(73) Assignee: Beckman Coulter, Inc., Brea, CA (US)

( * ) Notice: Subject to any disclaimer, the term of this patent is extended or adjusted under 35 U.S.C. 154(b) by 1303 days.

(21) Appl. No.: 12/029,257

(22) Filed: Feb. 11, 2008

(65) Prior Publication Data

US 2008/0286160 A1 Nov. 20, 2008

Related U.S. Application Data

(63) Continuation of application No. PCT/JP2006/315325, filed on Aug. 2, 2006.

(30) Foreign Application Priority Data

Aug. 10, 2005 (JP) .................................. 2005-232549
Aug. 10, 2005 (JP) .................................. 2005-232550

(51) Int. Cl.
*B01L 3/14* (2006.01)
(52) U.S. Cl.
USPC ........... 422/550; 422/547; 422/549; 220/252; 220/253; 220/263
(58) Field of Classification Search
USPC ......... 422/547, 548, 549, 550, 560, 561, 562; 220/253, 260, 262, 252, 263
See application file for complete search history.

(56) References Cited

U.S. PATENT DOCUMENTS

| | | | |
|---|---|---|---|
| 5,271,897 | A | 12/1993 | Wurschum et al. |
| 5,289,930 | A | 3/1994 | Inouye |
| 5,670,117 | A | 9/1997 | Erb et al. |
| 6,265,225 | B1 | 7/2001 | Otto et al. |
| 2004/0067090 | A1 | 4/2004 | Budds et al. |
| 2004/0170532 | A1 | 9/2004 | Takahashi et al. |

FOREIGN PATENT DOCUMENTS

| | | |
|---|---|---|
| JP | 57-185964 U | 11/1982 |
| JP | 5-281238 | 10/1993 |
| JP | 5-294354 | 11/1993 |
| JP | 8-58828 | 3/1996 |
| JP | 10-167309 | 6/1998 |
| JP | 11-194132 | 7/1999 |
| JP | 11-304805 | 11/1999 |
| JP | 2004-156971 | 6/2004 |
| JP | 2004-157020 | 6/2004 |
| JP | 2004-177254 | 6/2004 |
| JP | 2004-177255 | 6/2004 |
| JP | 2004-518588 | 6/2004 |
| JP | 2005-324832 | 11/2005 |
| WO | WO 98/31408 | 7/1998 |

*Primary Examiner* — Jill Warden
*Assistant Examiner* — Dwayne K Handy
(74) *Attorney, Agent, or Firm* — Kilpatrick Townsend & Stockton LLP

(57) ABSTRACT

A sealing member includes a sealing portion that is used for a cap attached to a reagent container and covers an opening of the cap with an open-close movement by flapping around a predetermined point. The sealing portion has, on an outer circumference in the predetermined point side, an extending portion that extends outward of the opening. The extending portion contacts with an upper edge of the opening when the sealing portion covers the opening.

19 Claims, 27 Drawing Sheets

SEALING MEMBER, CAP FOR REAGENT CONTAINER, AND REAGENT CONTAINER

CROSS-REFERENCE TO RELATED APPLICATIONS

This application is a continuation of PCT international application Ser. No. PCT/JP2006/315325 filed Aug. 2, 2006 which designates the United States, incorporated herein by reference, and which claims the benefit of priority from Japanese Patent Applications No. 2005-232549 and No. 2005-232550, both filed Aug. 10, 2005, incorporated herein by reference.

BACKGROUND OF THE INVENTION

1. Field of the Invention

The present invention relates to a sealing member, a cap for a reagent container, and a reagent container.

2. Description of the Related Art

In a conventional automatic analyzer, a number of open reagent containers are arranged along circumferential direction of a rotatable table provided in a reagent storage, and reagent is dispensed in a reactor vessel by rotating the table to a dispensing position. At this time, the automatic analyzer is placed in a condition, typically, such that the inside of the reagent storage is cooled to temperatures of 5 to 10° C. with a low humidity, to prevent degradation of reagent. Thus, in some conventional reagent containers, specially-structured caps are attached to the containers to prevent contained reagents from evaporation. (For example, Japanese patent application laid-open Nos. 2004-177255, H11-194132, and 2004-177254.)

SUMMARY OF THE INVENTION

A seating member of one aspect of the present invention includes a sealing portion that is used for a cap attached to a reagent container and covers an opening of the cap with an open-close movement by flapping around a predetermined point. The sealing portion has, on an outer circumference in the predetermined point side, an extending portion that extends outward of the opening. The extending portion contacts with an upper edge of the opening when the sealing portion covers the opening.

A cap for a reagent container of another aspect of the present invention is attached to a cylindrical opening of a main body containing a reagent, and includes a retainer that has an insertion cylinder connected to the cylindrical opening and that is attached to the cylindrical opening; a slide member that slidably fits in the retainer to cover the retainer and that has a flap member being raised and laid by the insertion cylinder according to a sliding motion against the retainer; a sealing member that is supported by the flap member and that seals an opening of the insertion cylinder with an open-close movement; and a biasing member that is placed between the retainer and the slide member to press the slide member toward the opposite direction from the retainer and that gives a pressing force to make the sealing member seal the opening of the insertion cylinder via the slide member. The sealing portion includes a sealing portion that has, on an outer circumference in a predetermined point side, an extending portion that extends outward of the opening, and an extending portion that contacts with an upper edge of the opening when the sealing portion covers the opening.

A reagent container of still another aspect of the present invention includes a cap attached to a cylindrical opening of a main body containing a reagent. The cap includes a retainer that has an insertion cylinder connected to the cylindrical opening and that is attached to the cylindrical opening; a slide member that slidably fits in the retainer to cover the retainer and that has a flap member being raised and laid by the insertion cylinder according to a sliding motion against the retainer; a sealing member that is supported by the flap member and that seals an opening of the insertion cylinder; and a biasing member that is placed between the retainer and the slide member to press the slide member toward the opposite direction from the retainer and that gives a pressing force to make the sealing member seal the opening of the insertion cylinder via the slide member. The sealing member is raised up along with the flap member by the insertion cylinder by sliding the slide member toward the retainer to open the opening.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
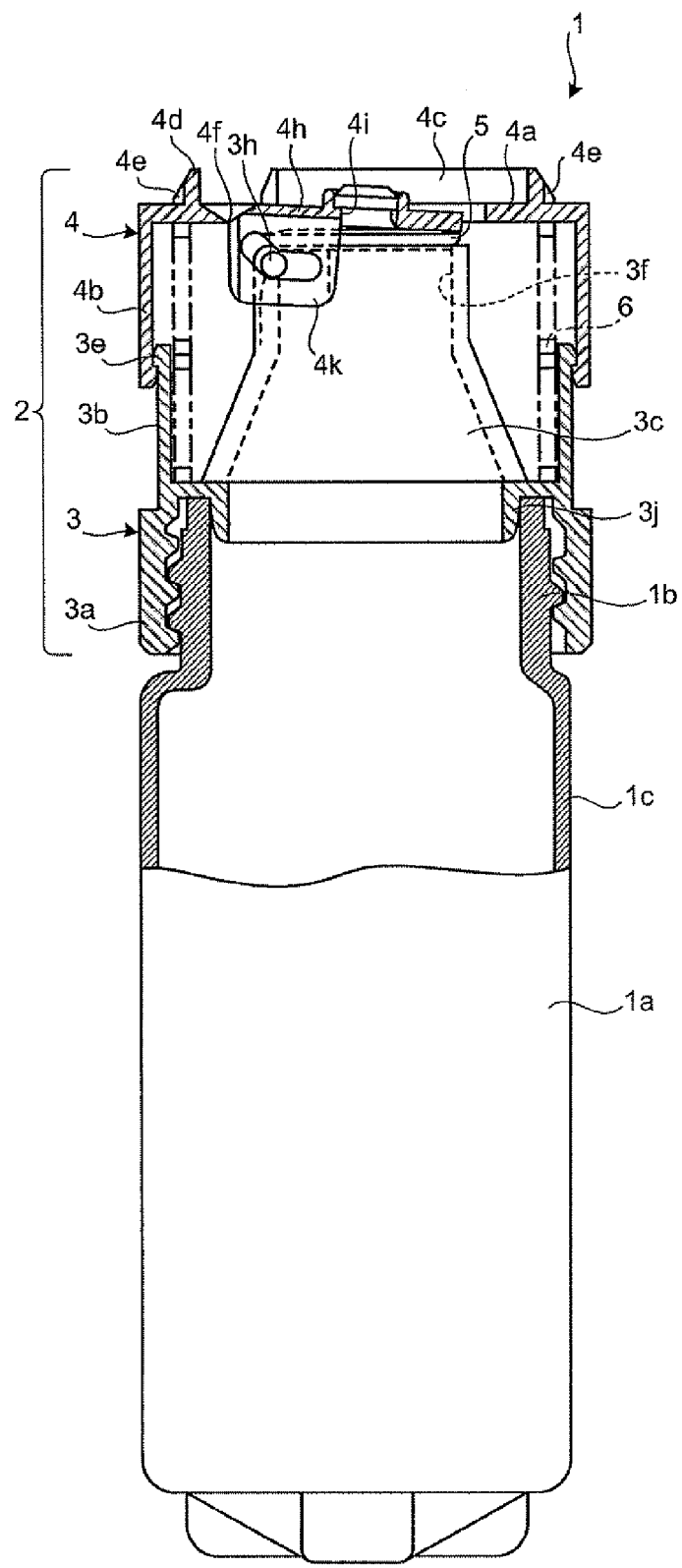
FIG. 1 is a front view of an upper part of a reagent container and a cross-section of a cap according to the present invention.
Figure 2:
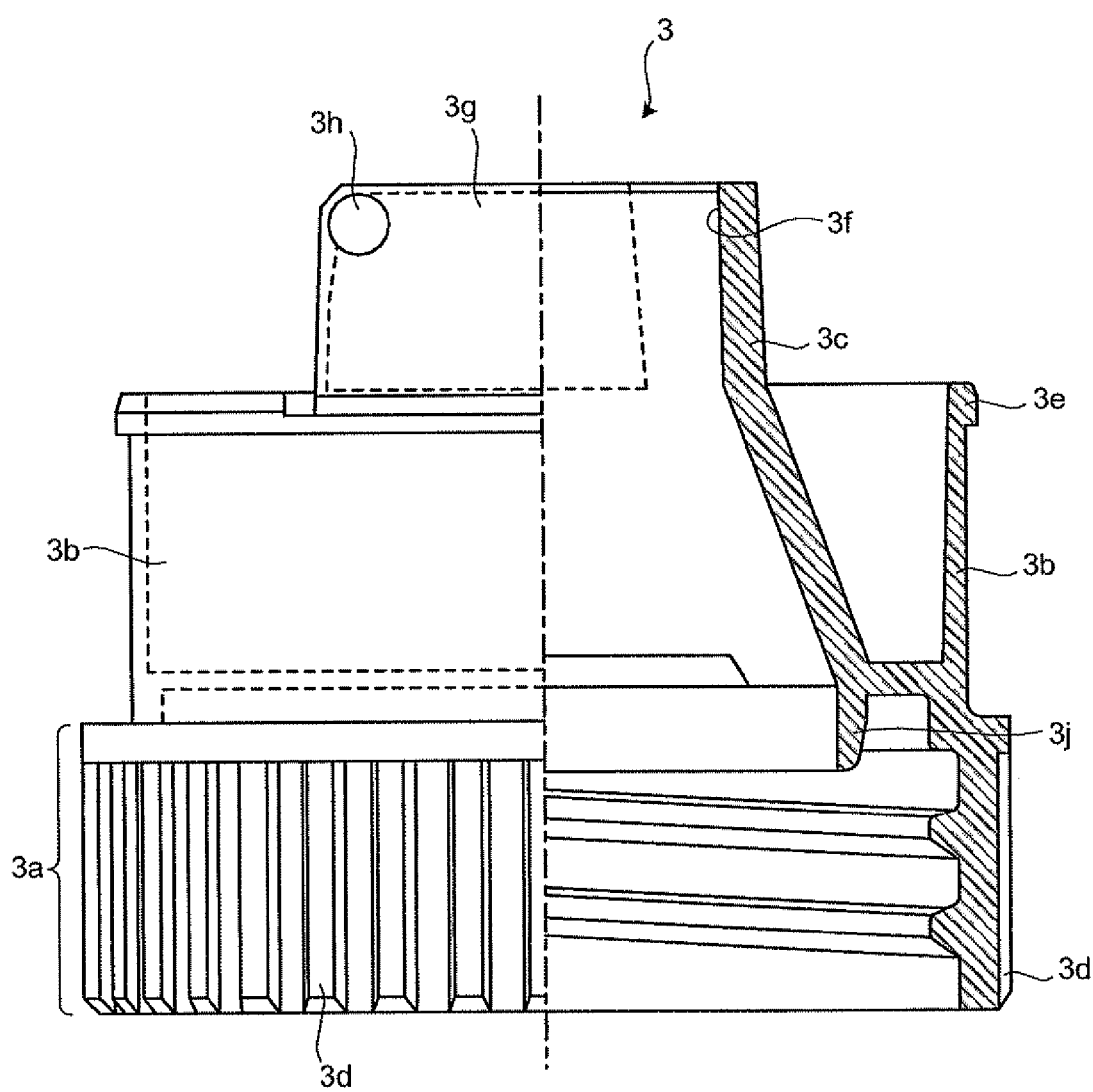
FIG. 2 is a front view showing a right-side half sectional view of a retainer constituting a cap of the present invention.
Figure 3:
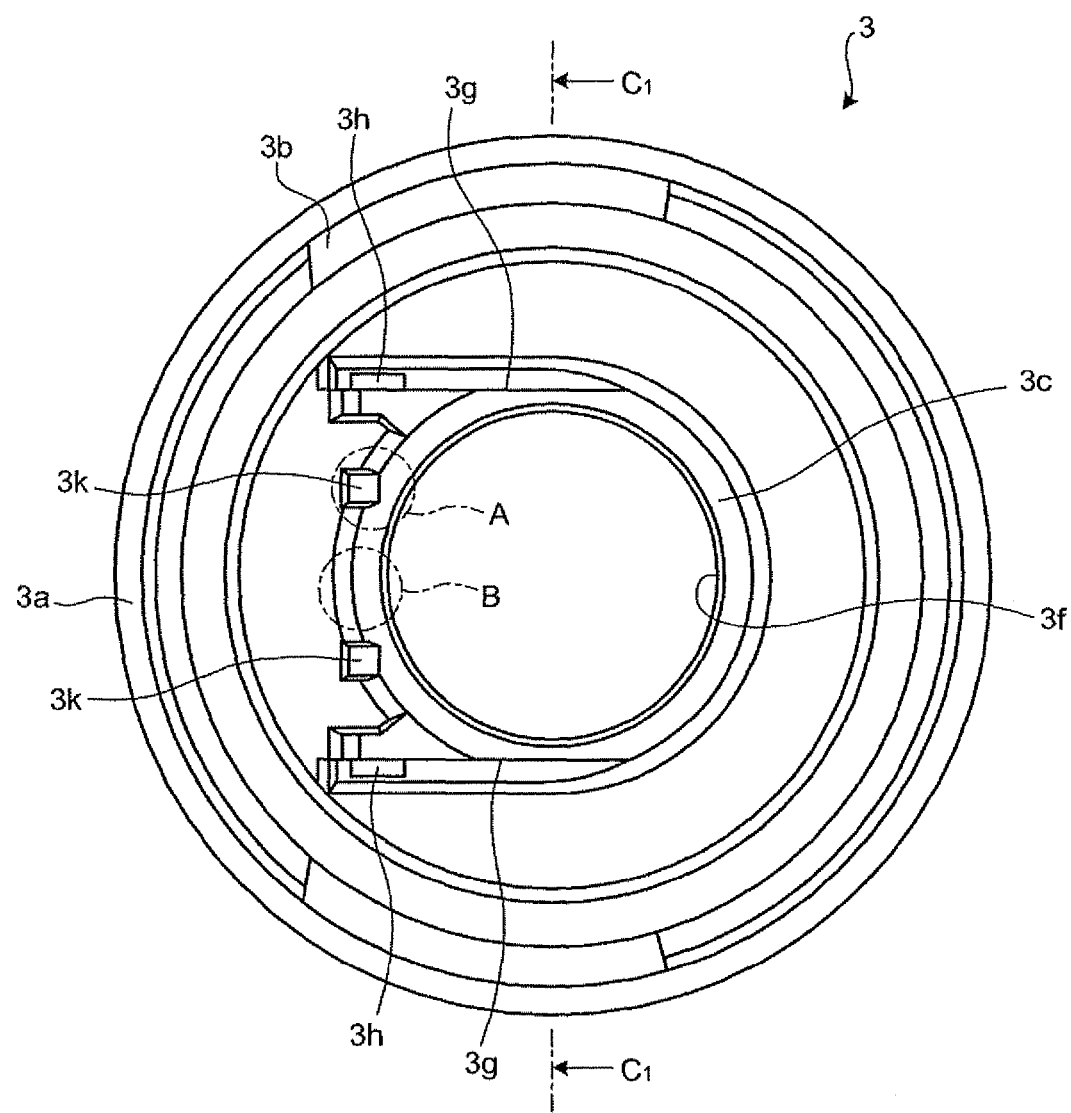
FIG. 3 is a plane view of the retainer.
Figure 4:
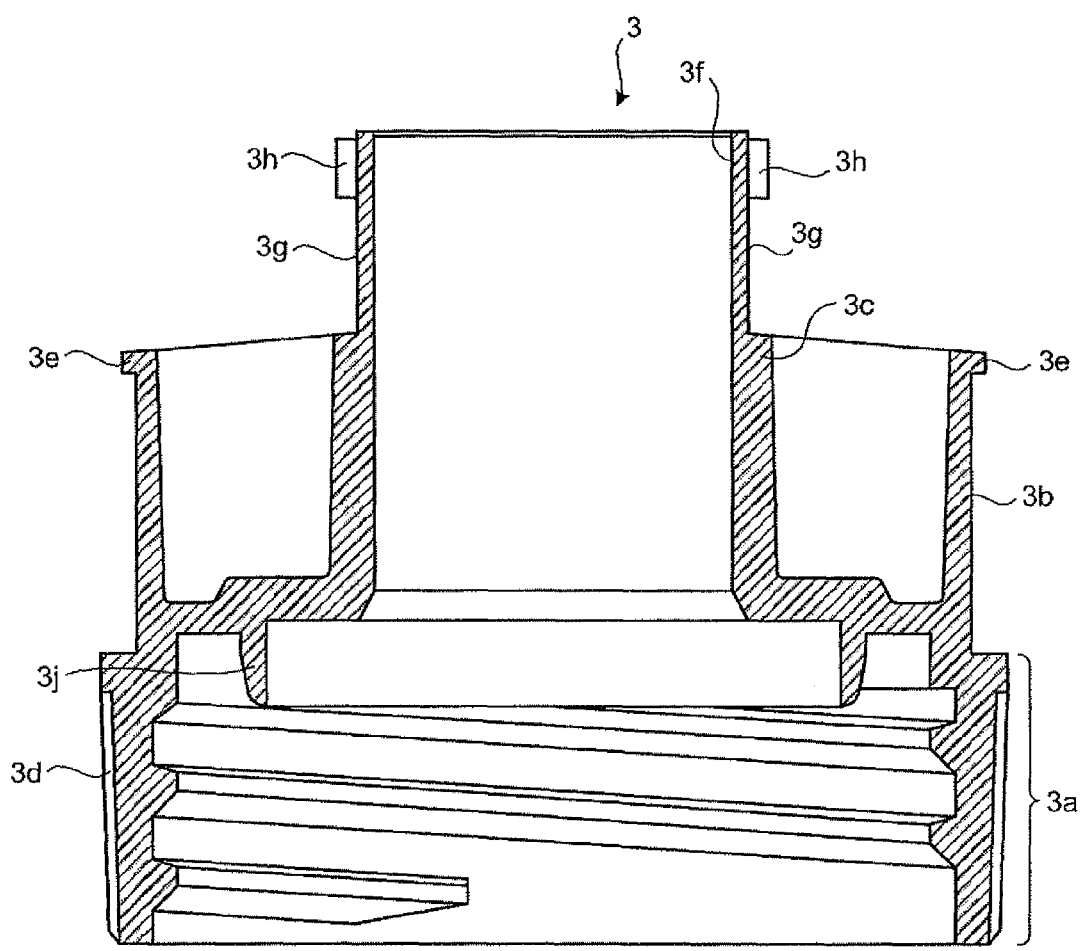
FIG. 4 is a cross-sectional view taken along the line C1-C1 of the retainer in FIG. 3.
Figure 5:
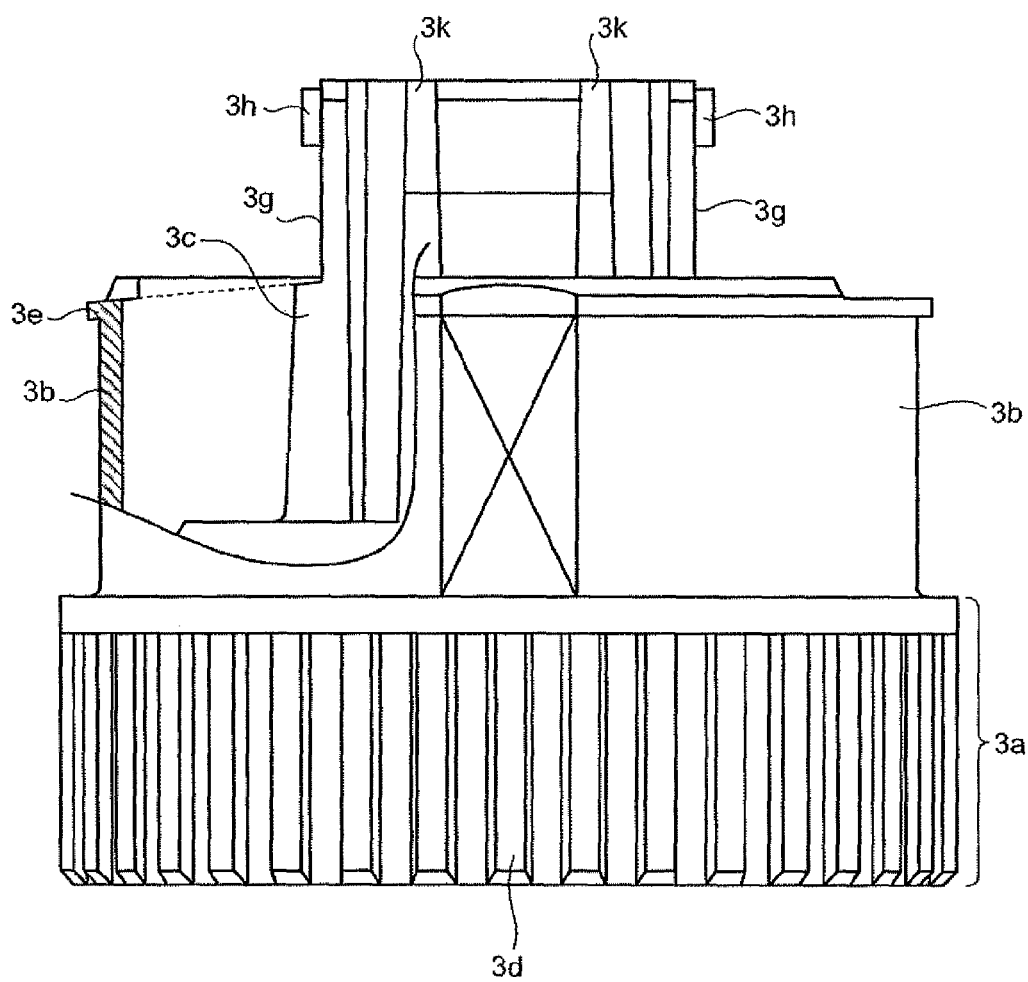
FIG. 5 is a left-side view of a partial cross-section of the retainer.
Figure 6:
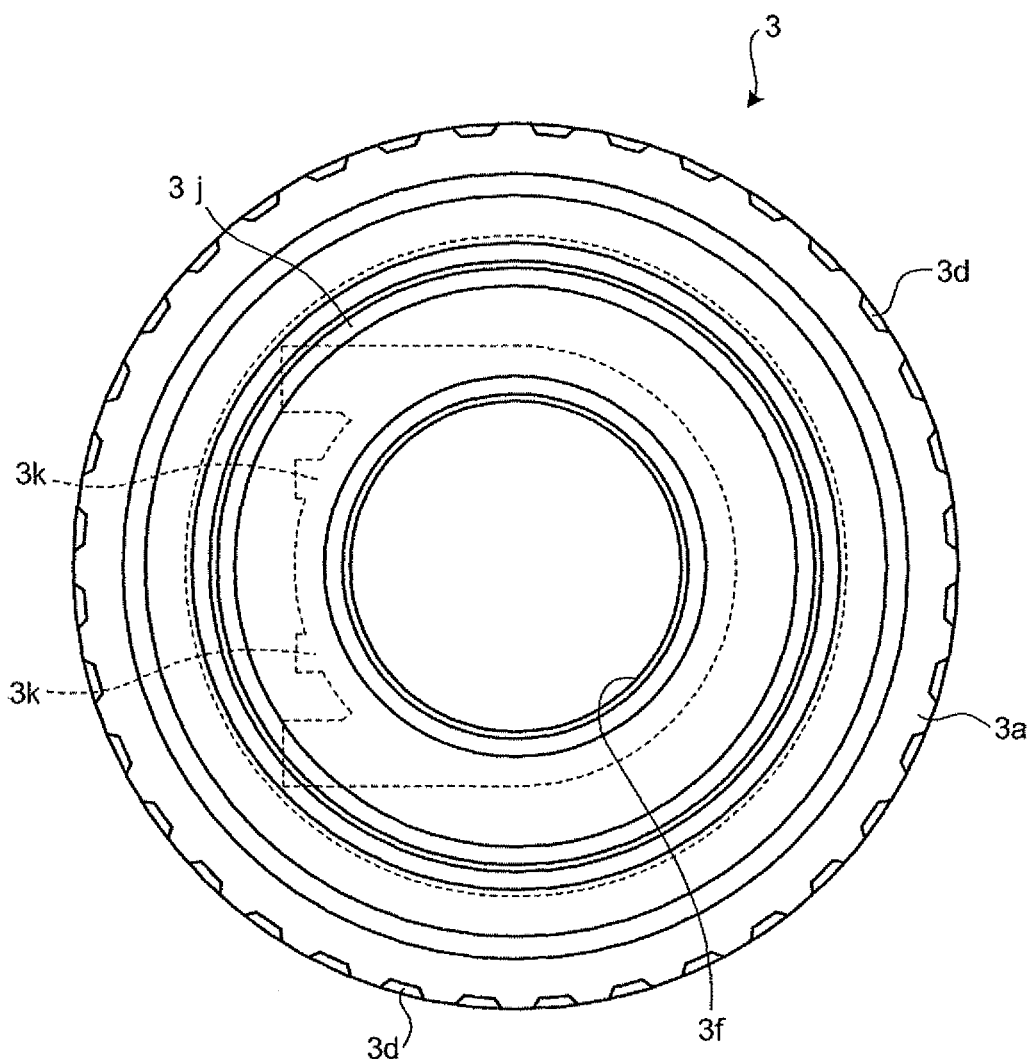
FIG. 6 is a bottom plan view of the retainer.

Exemplary embodiments of a seal member, a cap for a reagent container, and a reagent container according to the present invention are explained below with reference to the accompanying drawings. FIG. 1 is a front view showing the top of the reagent container and the cross-section of the cap. FIG. 2 is a front view showing right-side half sectional view of a retainer constituting the present invention. FIG. 3 is a plane view of the retainer. FIG. 4 is a cross-sectional view taken along the line C1-C1 of the retainer in FIG. 3.

A reagent container 1 is formed from a synthetic resin such as a high-density polyethylene (HDPE), and a cap 2 is attached to a cylindrical aperture 1b formed in an upper part of a main body 1a as shown in FIG. 1. The main body 1a is shaped like a cylinder, is provided with a flat portion 1c on a part of a side surface to attach an information label hereon, and is formed a male screw on an outer surface of the cylindrical aperture 1b. A type of reagent contained in the reagent container 1 or an expiration date is stored on the information label.

As shown in FIG. 1, the cap 2 includes a retainer 3, a slide member 4, a sealing member 5, and a biasing member 6, and seals the cylindrical aperture 1b of the reagent container 1 in such a manner that the cap 2 is openable and closable.

Figure 7:
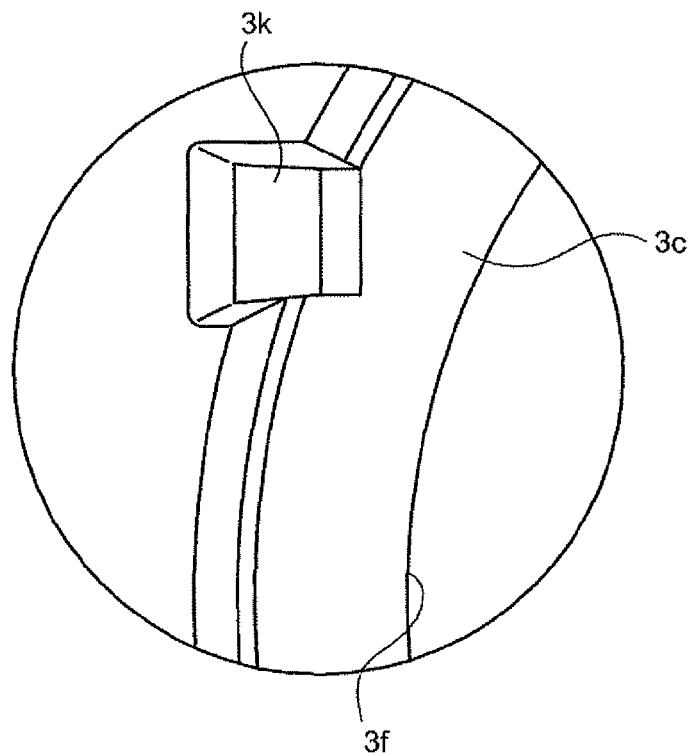
FIG. 7 is an enlarged view of Part A in FIG. 3.
Figure 8:
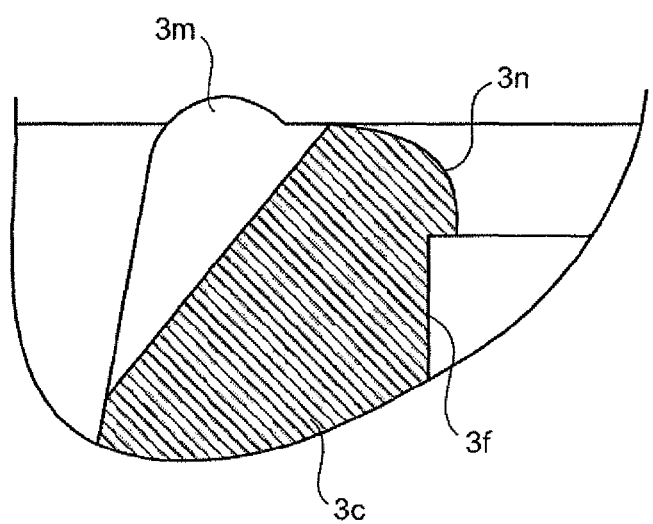
FIG. 8 is an enlarged cross-sectional view of Part B in FIG. 3.
Figure 9:
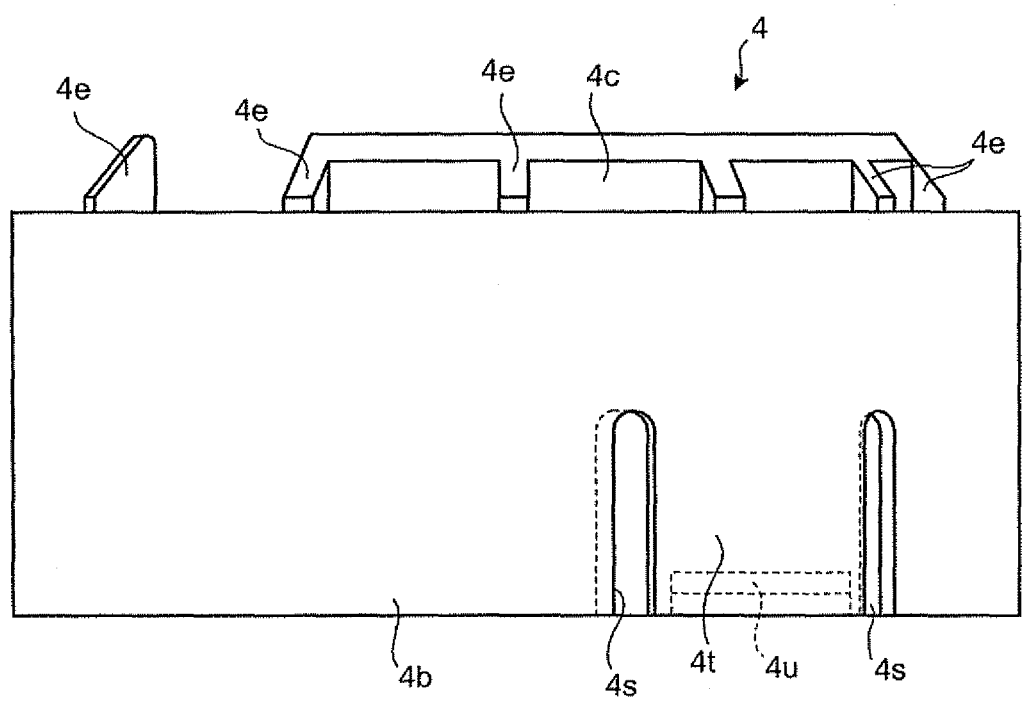
FIG. 9 is a front view of a slide member constituting the cap.

The retainer 3 is formed from a synthetic resin such as a polyethylene, and includes an attachment portion 3a that is attached to the cylindrical aperture 1b of the reagent container 1 by screwing, a guiding cylinder 3b that is linked to the attachment portion 3a, and an insertion cylinder 3c that is arranged in a center of the guiding cylinder 3b, as shown in FIGS. 1 to 8. The attachment portion 3a is provided with a knurling 3d that is adapted to be rotated by a fingertip (see FIGS. 2 and 5) on its outer surface, and a female screw on an inner surface. The guiding cylinder 3b is provided with an engaging portion 3e on an outer circumference of its upper side. The insertion cylinder 3c is communicated with the cylindrical aperture 1b at the bottom part, and is a cylinder in which a dispensing probe of the automatic analyzer is inserted from above. The insertion cylinder 3c is adapted to prevent evaporation and quality change of the reagent inside the regent container 1 and entry of a liquid from outside, by sealing an upper opening 3f with the sealing member 5 with a close-open motion. The insertion cylinder 3c is provided, on its upper part, with flat portions 3g in which portions to face each other are arranged to be parallel to one another, as shown in FIGS. 3 and 4. The flat portions 3g is provided, on the outer circumference of the upper part, with engaging protrusions 3h that are arranged at opposed positions across the center axis of the insertion cylinder 3c (see FIGS. 2 to 5). Also, the insertion cylinder 3c is provided, around the bottom, with a contact cylinder 3j that extends toward the attachment portion 3a and contacts with the inside of the cylindrical aperture 1b, as shown in FIGS. 2 and 4. The insertion cylinder 3c is provided with two ribs 3k as contact portions on the outer circumference of the upper part adjacent to the engaging protrusions 3h, as shown in FIGS. 3 and 7. The insertion cylinder 3c, as shown in FIG. 8, is provided with a protrusion 3m of which an inner circumference of an upper part is slightly projected upward between the two ribs 3k, and with a sealing portion 3n of which an inner circumference of an upper part is slightly bulged inward on all circumferences. The protrusion 3m and the sealing portion 3n are formed to have smooth surfaces without bumps since they contact with a bottom surface of a sealing portion 5g of the sealing member 5 to seal the upper opening 3f.

A slide member 4 is formed from a synthetic resin such as a polyethylene, is attached to the retainer 3 to freely slide in the vertical direction by fitting it into the retainer 3 from above, and covers the top of the retainer 3. In the slide member 4, as shown in FIGS. 1 and 9 to 15, a slide cylinder 4b is vertically and integrally fixed to an outer circumference of a top panel 4a. In the slide member 4, the sealing member 5 is held by a flap member 4h.

Figure 10:
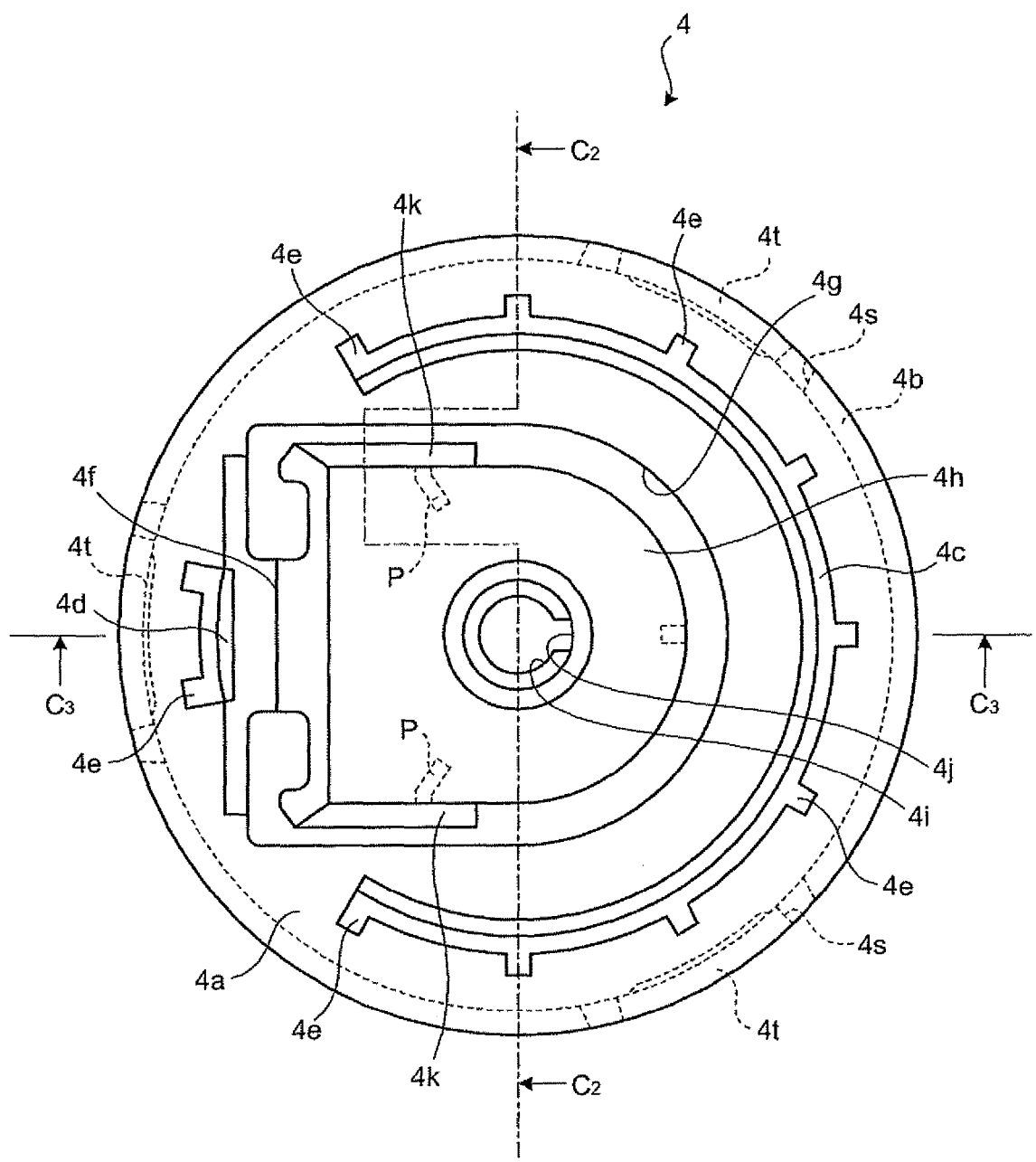
FIG. 10 is a plane view of the slide member.
Figure 11:
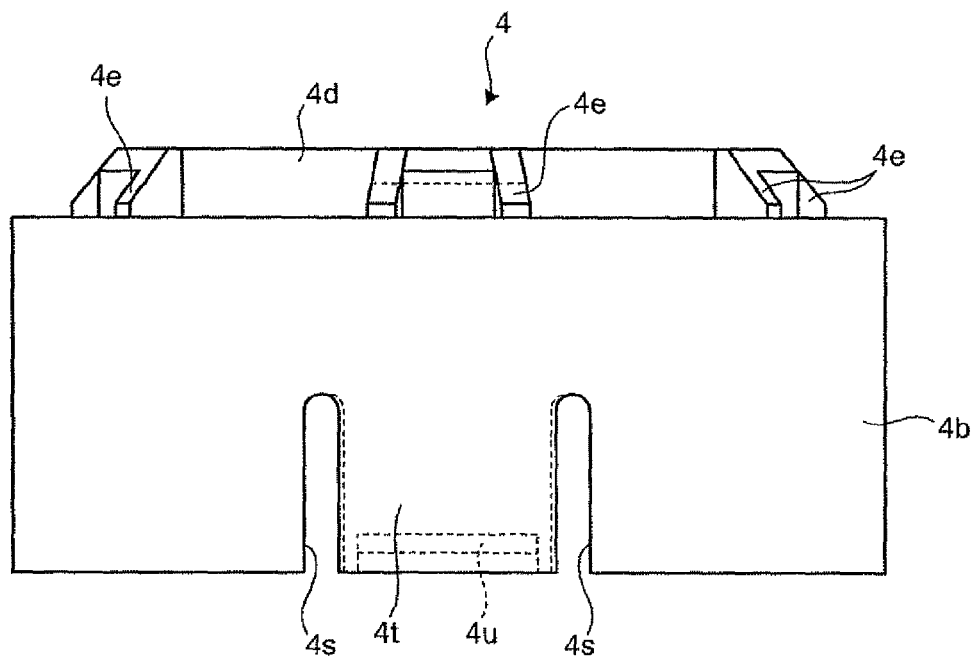
FIG. 11 is a left-side view of the slide member.
Figure 12:
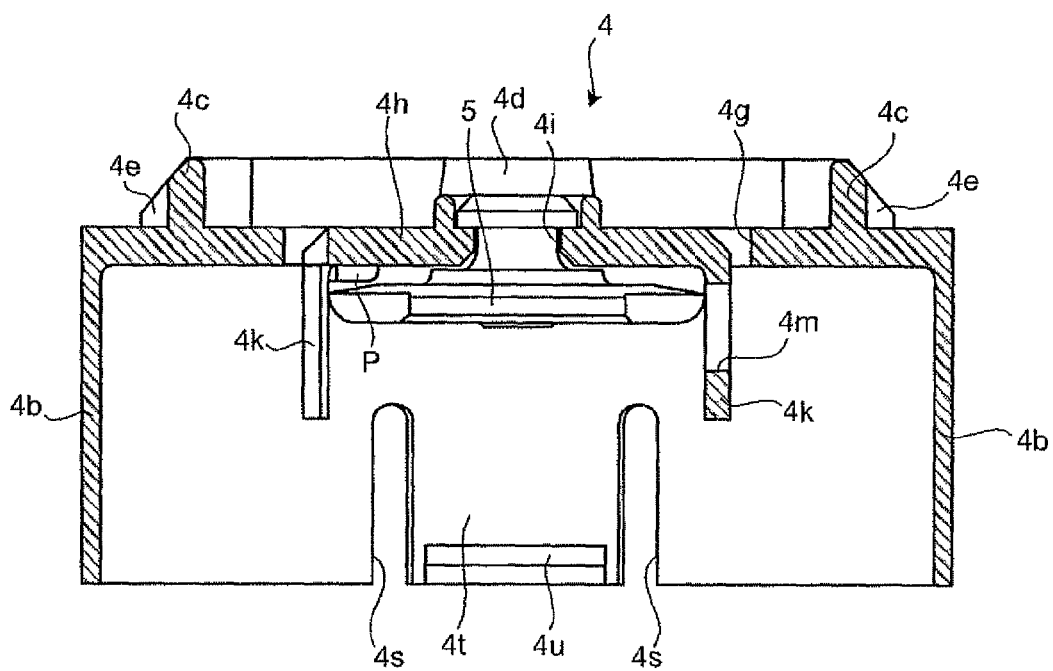
FIG. 12 is a cross-sectional view taken along the line C2-C2 of the slide member in FIG. 10.

The top panel 4a is provided with convex portions 4c, 4d along a circumference near the outer circumference of the upper part. The convex portion 4c is configured to be longer than the convex portion 4d. Each convex portion 4c, 4d is provided, on the outer circumferences, with a plurality of position control ribs 4e that is arranged in a radial pattern and becomes gradually lower outward. The plurality of position control ribs 4e, as shown in FIG. 10, are arranged on the circumference of the same radius center which is an insertion hole 4i. Also, the top panel 4a is provided, at its center, with the flap member 4h formed by an opening 4g and a hinge 4f of which a portion adjacent to the convex portion 4d is thin-walled. The flap member 4h has at its center the insertion hole 4i in which the sealing member 5 is inserted. Here, the insertion hole 4i is provided with a concave 4j that positions the sealing member 5 on the opposite side facing the hinge 4f (see FIGS. 10 and 14). Also, the flap member 4h is provided with guiding piece 4k that is vertically attached to the flap member 4h and guides the raising and laying of the flap member 4h to the position facing each other adjacent to the hinge 4f. Furthermore, the flap member 4h is provided with a protrusion P disposed on the both side of bottom surface between the hinge 4f and the insertion hole 4i in the radial direction centering the insertion hole 4i (see FIGS. 10 and 14).

Figure 13:
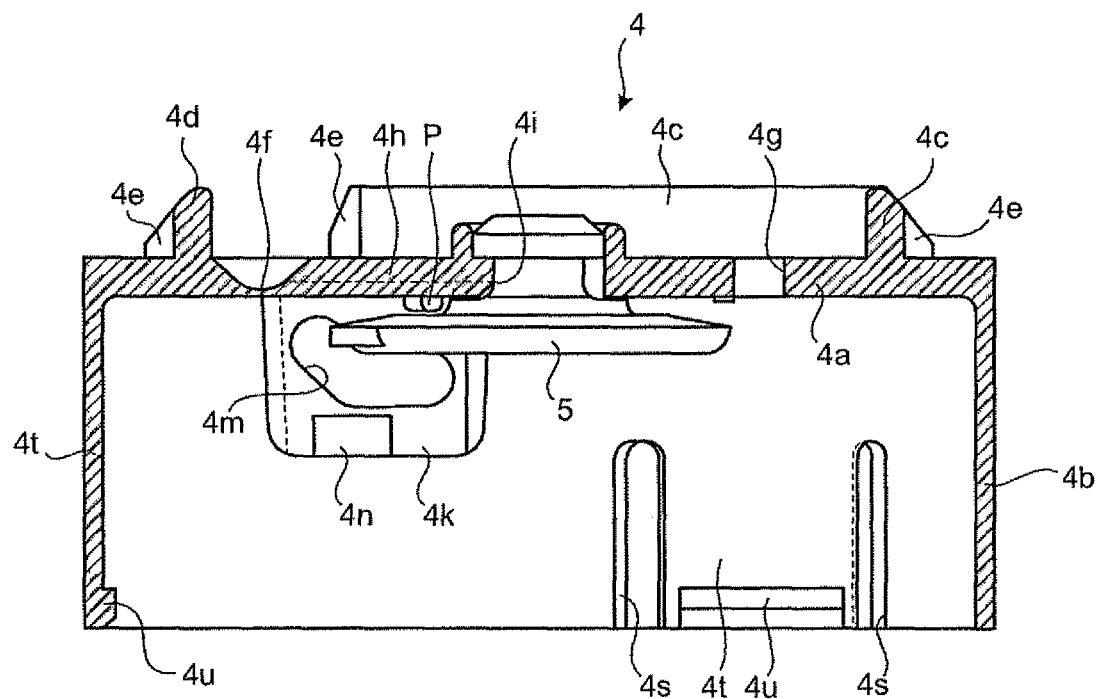
FIG. 13 is a cross-sectional view taken along the line C3-C3 of the slide member in FIG. 10.
Figure 14:
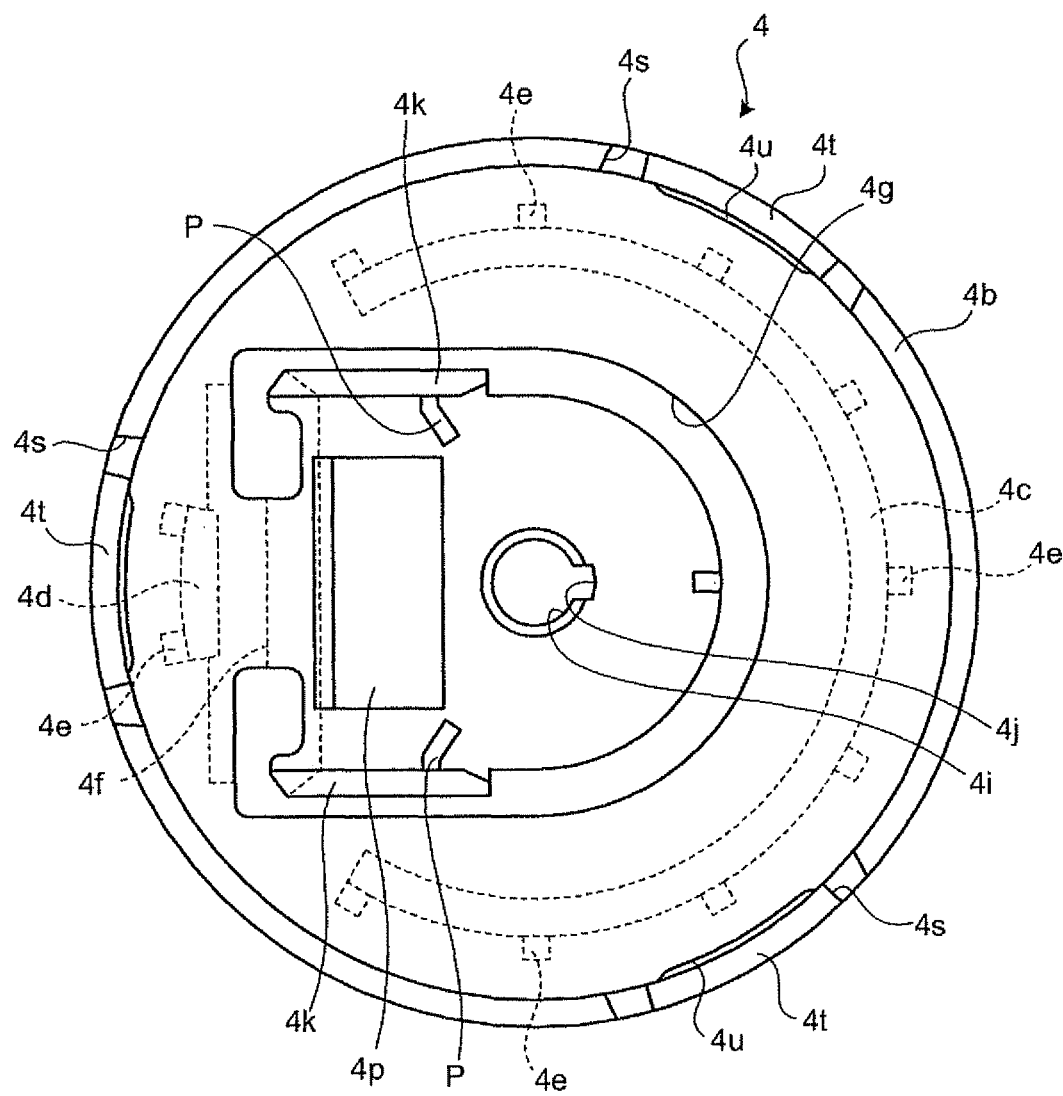
FIG. 14 is a bottom view of the slide member.
Figure 15:
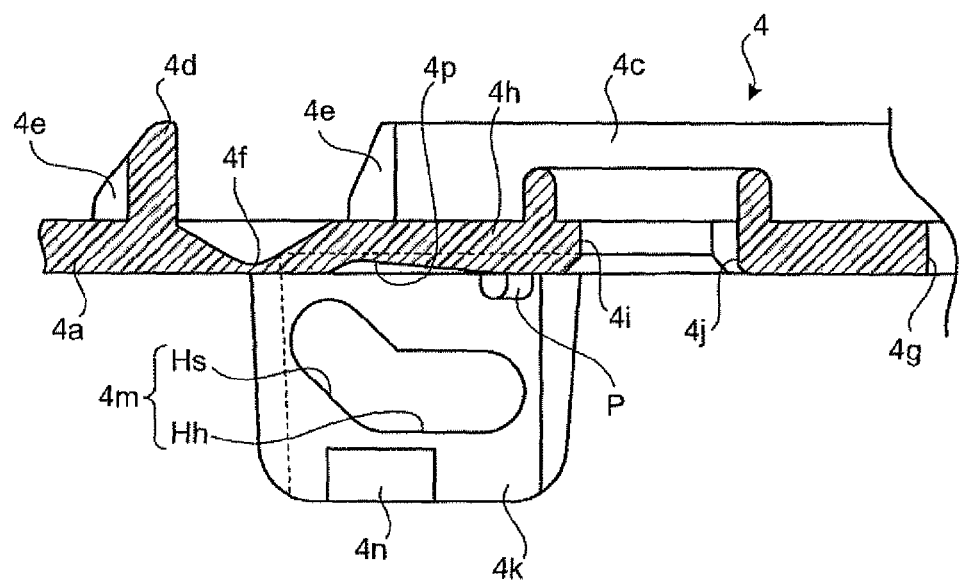
FIG. 15 is an enlarged view of the upper part of FIG. 13.

The guiding piece 4k is provided with a guiding hole 4m that engages with an engaging protrusion 3h of the retainer 3 (see FIGS. 13 and 15). The guiding hole 4m, as shown in FIG. 15, is composed of a long hole Hh that extends in the horizontal direction to the top panel 4a and a long hole Hs that is inclined to the plane of the top panel 4a. Also, two guiding pieces 4k, as shown in FIG. 15, is provided with a slanted ditch 4n disposed in a facing position that is deep in the hemline side and becomes shallower toward the guiding hole 4m. The slanted ditch 4n leads the engaging protrusion 3h provided in the retainer 3 to the guiding hole 4m. Furthermore, the flap member 4h, as shown in FIGS. 14 and 15, is provided with a concave 4p that is slightly concaved between the hinge 4f and the insertion hole 4i on the under surface. The concave 4p regulates the movement, when the sealing member 5 is raised or laid together with the flap member 4h to open or close the upper opening 3f, such that the slanted portion 5k of the sealing member 5 does not contact with the under surface of the flap member 4h. Here, a ditch instead of a long hole could be used for the guiding piece 4k as long as engaging with the engaging protrusion 3h.

The slide cylinder 4b is arranged on the outer circumference of the guiding cylinder 3b, and is provided with the bottom engaging pieces 4t via slits 4s at three places along the circumferential direction as shown in FIGS. 9 and 11 to 14. Each engaging piece 4t, by putting a protrusion 4u inside the bottom part and the engaging portion 3e formed on the outer circumference of the upper part of the guiding cylinder 3b in engagement, regulates the raising position of the slide member 4 and regulates so that the slide member 4 does not uncouple from the retainer 3.

Figure 16:
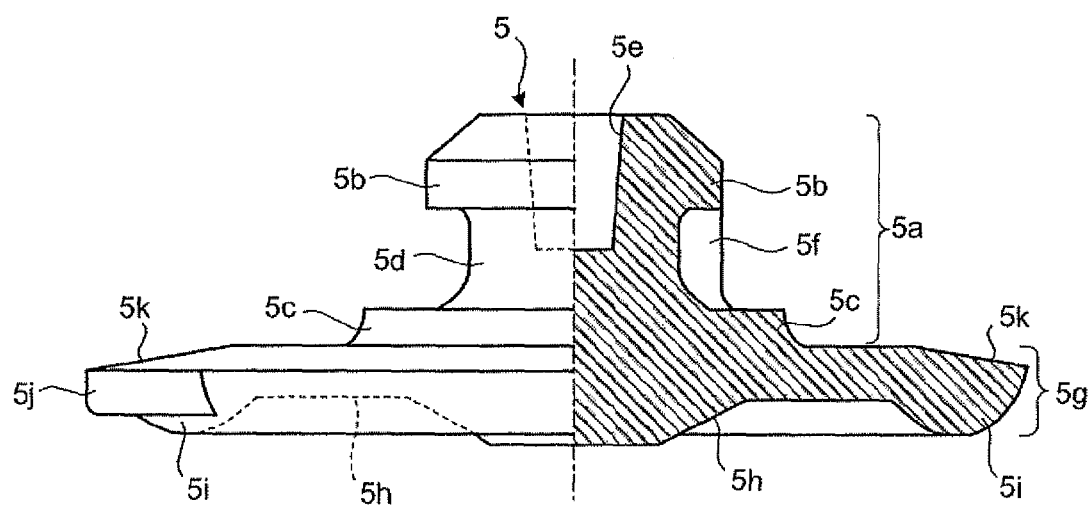
FIG. 16 is a front view showing a right-side half sectional view of the sealing member, of the present invention, constituting the cap.
Figure 17:
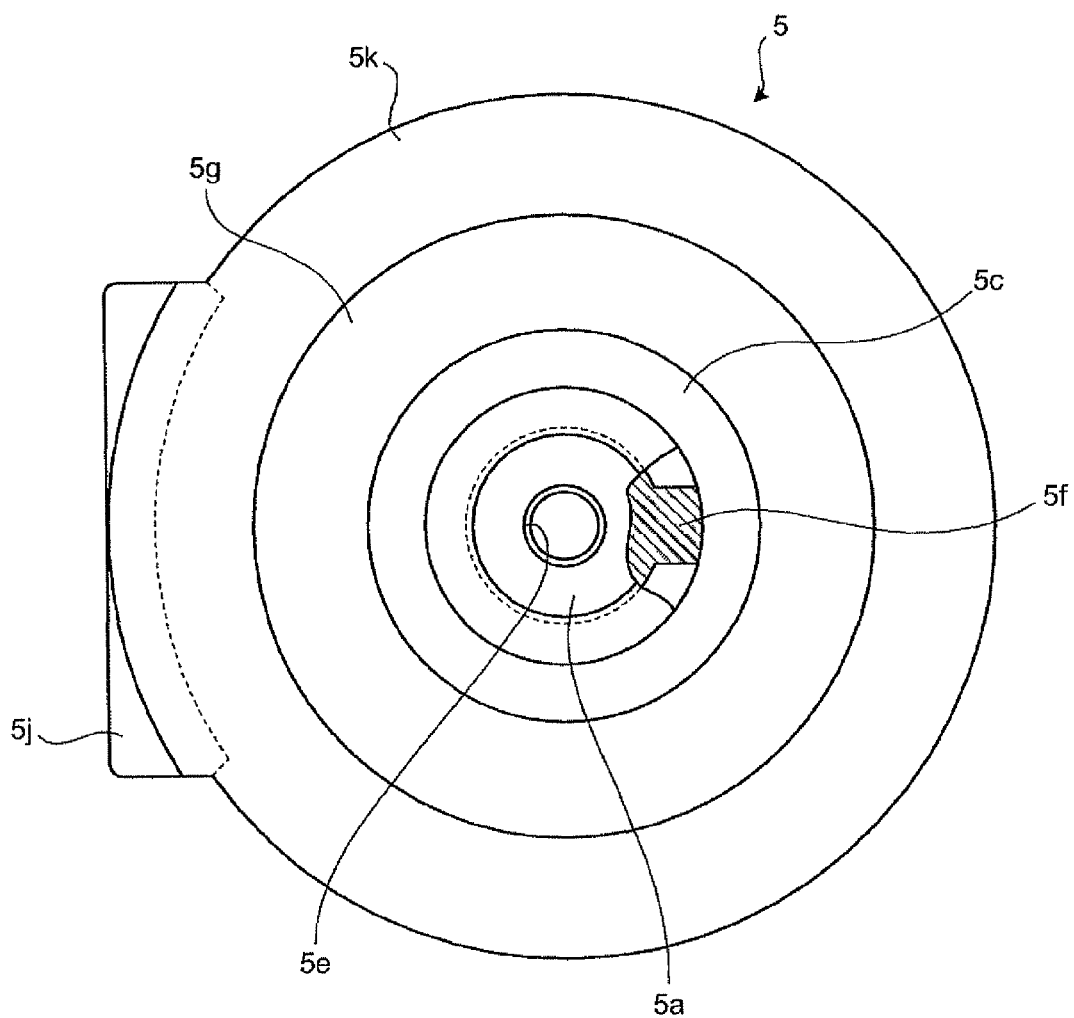
FIG. 17 is a plane view of a partial cross-section of the sealing member.
Figure 18:
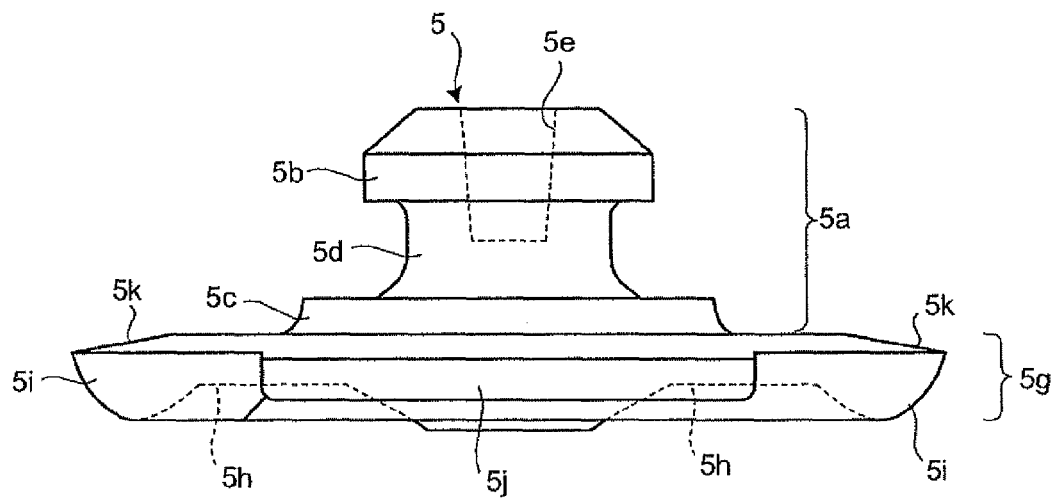
FIG. 18 is a left-side view of the sealing member.
Figure 19:
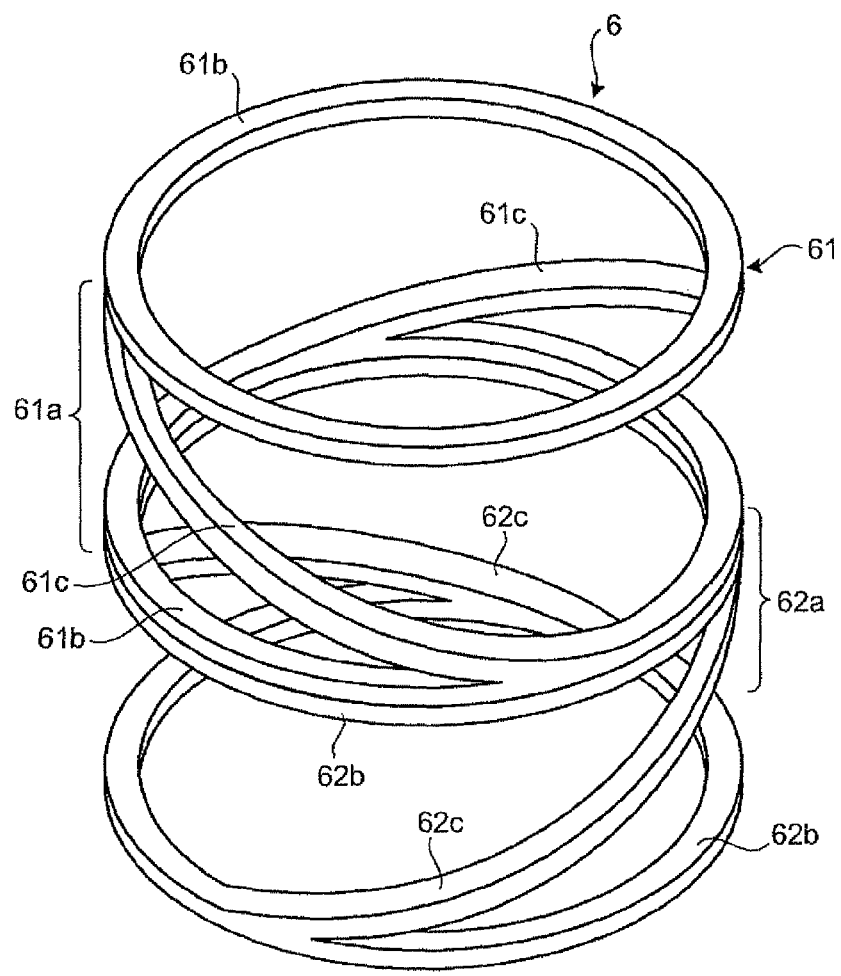
FIG. 19 is a perspective view of a biasing member constituting the cap.
Figure 20:
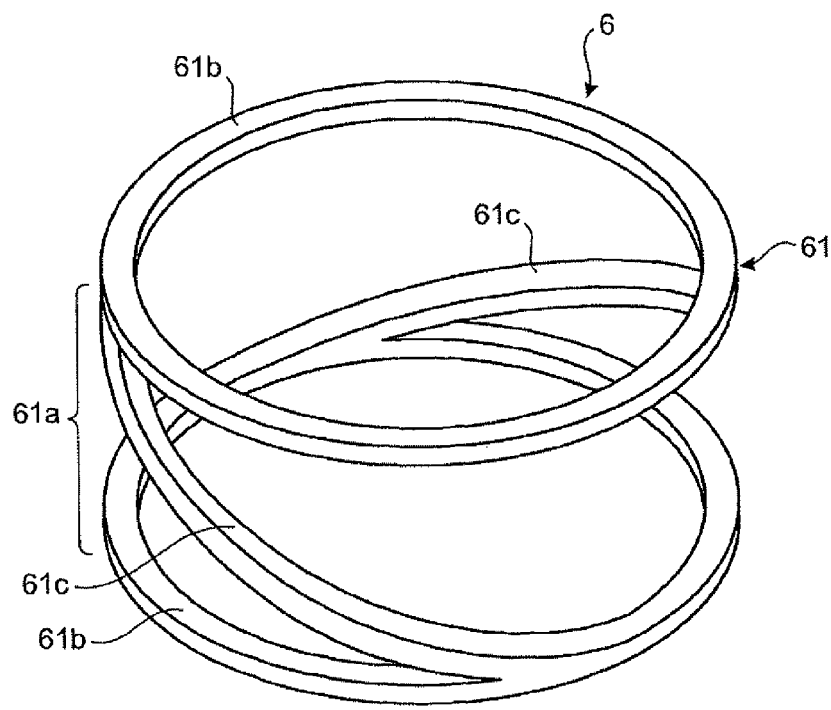
FIG. 20 is a perspective view showing a side of a spring forming the biasing member.

The sealing member 5, for example, is formed from a synthetic resin having elasticity such as an ethylene-polyethylene terpolymer (EPUM), seals the upper opening 3f of the retainer 3 by being held by the flap member 4h, and opens and closes the upper opening 3f by raising and laying the flap member 4h. The sealing member 5, as shown in FIGS. 16 to 18, includes a holding portion 5a and a sealing portion 5g. The holding portion 5a is provided with a small diameter portion 5d between an upper locking part 5b and a lower locking part 5c, and is provided with a disk-shaped sealing portion 5g under the lower locking part 5c. Also, the holding portion 5a is provided with a bore 5e that is bored from the level of the upper locking part 5b to the level of midway between the upper locking part 5b and the small diameter portion 5d, at the radial center the upper locking part 5b. The holding portion 5a can be easily deformed in the upper locking part 5b to the small diameter portion 5d because of the bore 5e, and thus can be easily attached to the insertion hole 4i formed in the flap member 4h. Also, the holding portion 5a is provided with a positioning rib 5f that guides a concave 4j of the flap member 4h to fit in the small diameter portion 5d in order to position a flange 5j in the hinge 4f side.

On the other hand, the sealing portion 5g has a diameter between the inner diameter of the upper opening 3f and the outer diameter of the upper part of the insertion cylinder 3c, and a slanted portion 5k that becomes lower toward the outward of the outer circumference of the upper part. The slanted portion 5k is formed on the outer circumference of the upper surface of the sealing portion 5g to put in the position of the concave 4p when the sealing member 5 is attached to the flap member 4h (see FIGS. 14, 15). The sealing portion 5g is provided with a seal convex 5i that bulges downward on the outer circumference of the bottom part, which is formed by the concave 5h arranged along the circumferential direction toward the radial center of the bottom surface. The sealing portion 5g is also provided, on the opposed side that faces with the positioning rib 5f across the bore 5e, with the quadrangular flange 5j that extends outward in the radial direction. In the sealing member 5, the flange 5j is placed on the side of the hinge 4f by engaging the positioning rib 5f with the concave 4j, and the flange 5j contacts with the upper edge of the upper opening 3f and the upper surface of two ribs 3k arranged on the outer circumference of the upper part of the insertion cylinder 3c when the flap member 4h is raised or laid. Therefore, flange 5j regulates the movement such that the side of the hinge 4f of the sealing portion 5g does not fall into the upper opening 3f when the flap member 4h is raised or laid. Thus, for the flange 5j, the length of extension toward the hinge 4f is determined by considering the distance by which the upper opening 3f of the sealing member 5 shifts outward in the radial direction along with the raising and laying motion of the flap member 4h. In the sealing member 5, the sealing portion 5g is given elasticity by forming the concaves 5h, the seal convex 5i adheres tightly to the sealing portion 3n (see FIG. 8).

The biasing member 6 is arranged between the retainer 3 and the slide member 4, and biases the slide member 4 upward to separate the slide member 4 from the retainer 3. The biasing member 6 is a coil spring that applies a pressing force to the sealing member 5 to seal the upper opening 3f. The biasing member 6 is formed from a synthetic resin such as a polyacetal resin (POM), and formed by stacking two spring units 61 and a spring unit 62, as shown in FIGS. 19 to 22.

The spring units 61 includes ring-shaped supporting members 61b disposed in the both side of a coil portion 61a and the coil portion 61e. The coil portion 61a has a turning number of a ½. Two coil member 61c, which turns in a right-handed direction, is connected to the supporting members 61 disposed on their both sides in such a manner that their joining are arranged in symmetrical positions (an angle of 180°) on their circumferences. Each supporting member 61b is provided with protrusions 61d (see FIG. 22) at a plurality of positions of the bottom surface.

Figure 21:
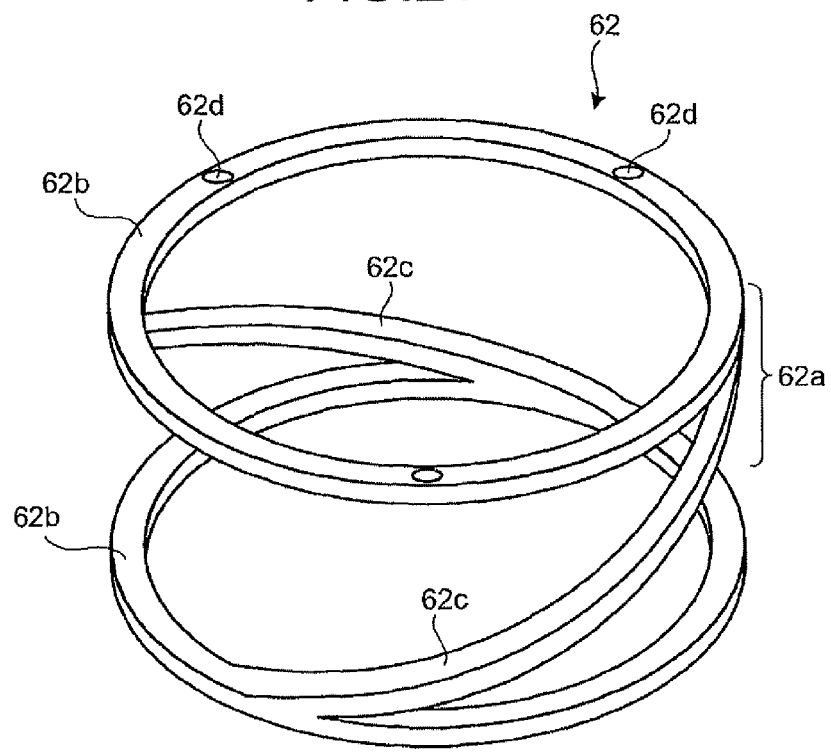
FIG. 21 is a perspective view showing the other side of the spring forming the biasing member.

The spring unit 62, as shown in FIG. 21, includes a coil portion 62a and a supporting portion 62b, and is configured almost the same as the spring unit 61. However, unlike the spring unit 61, the spring unit 62 is provided with two coil members 62c that turns in the left-handed direction, and the supporting portion 62b disposed in the upper part includes concaves 62d (see FIGS. 21 and 22) at a plurality of positions on the upper surface. The concaves 62d position the spring unit 61 and the spring position 62 such that the spring unit 61 comes, along the circumference, ahead of the spring position 62 by 90° when the concaves 62d engage with the protrusions 61d.

Here, a force exerted by the spring units 61, 62 is increased by giving a greater pitch angle than 20° or a greater turning number than ½. However, if done so, the coil member 61c, 62c of the spring units 61, 62 tend to bulge outward from the central axis in the radial direction when compressed. If the bulging of the spring units 61, 62 occurs, the outer surface of the spring units 61, 62 that bulge outward contacts with the inner surface of the guiding cylinder 3b of the retainer 3 or the slide cylinder 4b of the slide member 4, so the function of the spring units 61, 62 is harmed, and the force exerted by the springs is weaken by these contact or friction caused by the contacts. However, the spring units 61, 62 cannot have an enough spring force if the tuning number or the pitch angle is too small.

Figure 22:
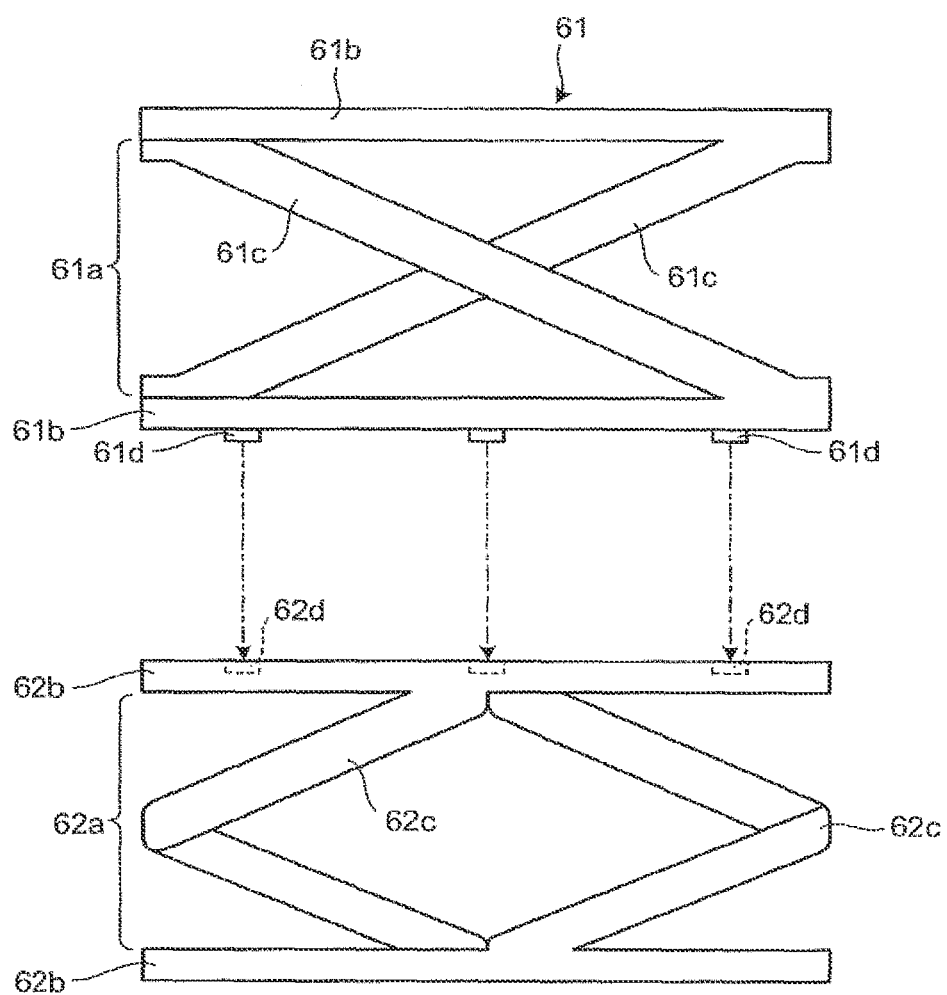
FIG. 22 is a front view showing a combination of two springs to form the biasing member.

The biasing member 6, as shown in FIG. 22, is manufactured by stacking the spring unit 61 and the spring unit 62, and by engaging the concaves 62d with the corresponding protrusions 61d respectively. The biasing member 6 can be made by bonding, with bond, the supporting portion 61b and the supporting portion 62b of the spring unit 61 and the spring unit 62, respectively, that face each other. Also, if the spring unit 61 and the spring unit 62 are used by themselves, the coil member 61b and the coil member 62b may rotate according to the turning direction of the coil member 61c, 62c when expanded or contracted by applying force. However, like the biasing member 6 which is made by stacking the spring unit 61 and the spring unit 62, each having a different turning direction, the rotational force is balanced out because the supporting portion 61b and the supporting portion 62b attempt to rotate in the different rotational directions although the supporting portion 61b and the supporting portion 62b rotate when expanded or contracted. Therefore, the biasing member 6 prevents the supporting portions 61b, 62b from rotational frictions to eliminate constraints for the expansion and contraction function of the coil members 61c, 62c, thus the biasing member 6 can effectively function as a spring.

Figure 23:
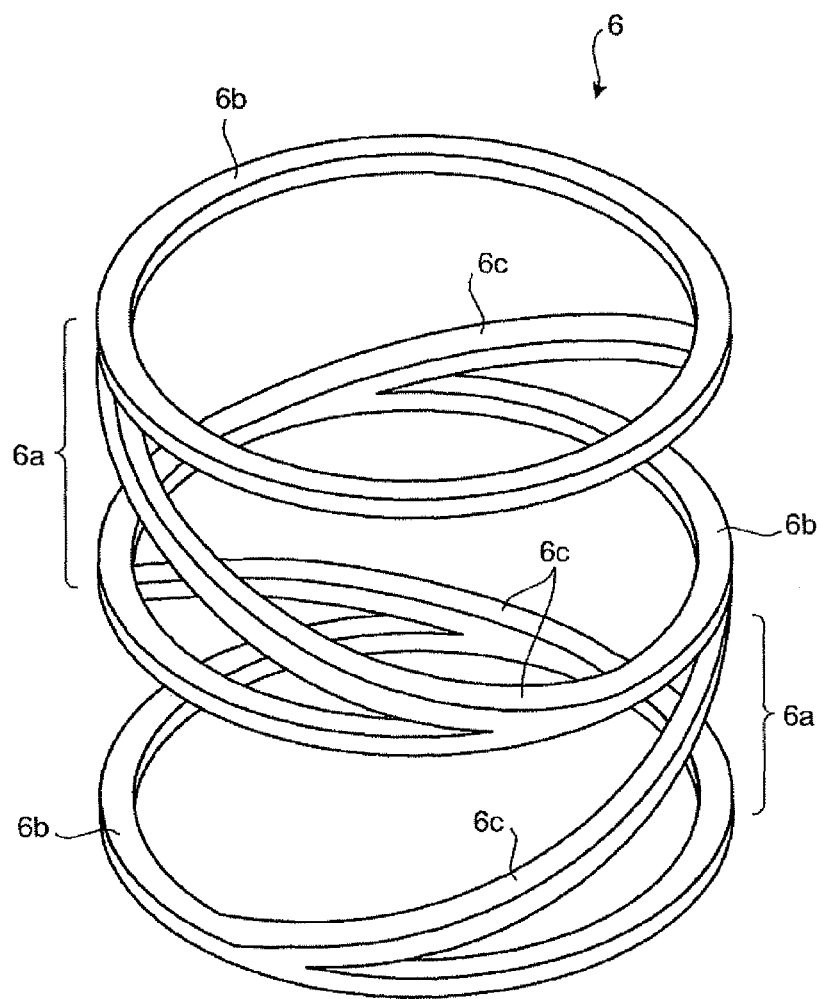
FIG. 23 is a perspective view of another example of a biasing member.

Here, if the biasing member 6 is made up by alternately stacking an odd number of the coil members 61c, 62c such that the turning direction of each coil member is different from that of the adjacent coil member, the aliquant coil member 61c, 62c is set to have a pitch angle of 20 degrees or below. By this way, the biasing member 6 can suppress the rotation of the supporting portion 61b and the supporting portion 62b caused by the aliquant coil member. Meanwhile, the biasing member 6 is formed from a synthetic resin. As shown in FIG. 23, two coil portions 6a are connected to three ring-shaped supporting portions 6b, and the turning direction of two coil members 6c can be the opposite directions, a right-handed direction and a left-handed direction, for each coil portion 6a.

The reagent container 1 configured as described above is attached with the cap 2 by screwing the attachment portion 3a in the cylindrical aperture 1b after disposing the biasing member 6 on the inner circumference of the guiding cylinder 3b and assembling the cap 2 by attaching the slide member 4 to the retainer 3 from above. Thus, the cap 2 can be easily assembled.

At this time, the sealing member 5 contacts with the upper edge of the upper opening 3f, and is provided, on the outer circumference of the sealing portion 5g, with the flange 5j as an extending part that extends outward of the upper opening 3f. Therefore, when raised and laid along with the flap member 4h, the sealing member 5 regulates the flange 5j to contact with the upper edge of the upper opening 3f and the sealing portion 5g not to fall into the upper opening 3f, so that the sealing member 5 causes a smooth opening and closing. Also, the cap 2 with the sealing member 5 has a simpler structure as compared with a conventional cap, and costs less to manufacture because of a fewer number of parts.

Also, since the retainer 3 is provided with the knurling 3d on the outer surface of the attachment portion 5a, one can easily screw the attachment portion 3a into the cylindrical aperture 1b with his finger tips. On the other hand, since the slide member 4 is provided with the engaging pieces 4t via the slits 4s at three sections of bottom part of the slide cylinder 4b, the protrusion 4u can easily engage with the engaging portion 3e formed on the upper part of the guiding cylinder 3b of the retainer 3. Thus, the slide member 4 can freely slide along the guiding cylinder 3b between the attachment portion 3a and the engaging portion 3e without running off the retainer 3 although the biasing member 6 pushed the slide member 4 upward to separate from the retainer 3. Also, since the slide member 4 is provided with the slanted ditches 4n inside the guiding piece 4k that faces to one another, when the slide member 4 is put on the retainer 3, the engaging protrusions 3h are guided by the corresponding slanted ditches 4n and smoothly engage with the guiding holes 4m. Also, since the reagent container 1 including the biasing member 6 is all formed from a synthetic resin, it has an advantage that scraping is easily done because there is no need to collect a coil spring made of metal, compared with a conventional reagent container with a metallic coil spring as a biasing member.

Figure 24:
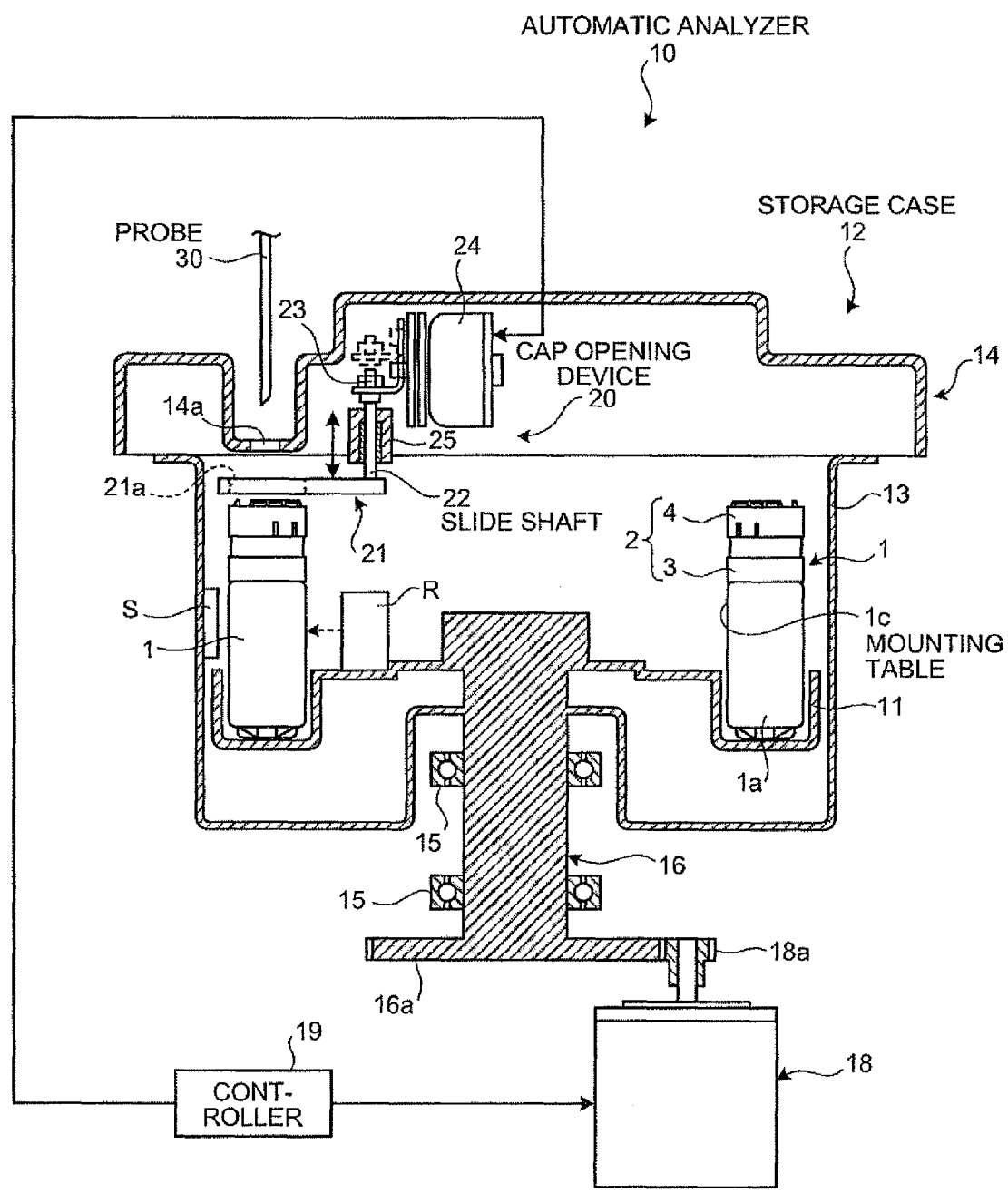
FIG. 24 is a schematic view of an automatic analyzer to which the reagent container of the present invention is applied.

Next, an automatic analyzer 10 using the reagent container 1 configured as described above will be explained with reference to FIG. 24. The automatic analyzer 10 includes a mounting table 11 that holds a plurality of the reagent containers 1 in a circle thereon and rotates, storage case 12 that keeps the plurality of reagent containers 1 on the mounting table 11 at a certain temperature (for example, 5 to 10° C.) by a cooling means (not shown in figures), a cap opening device 20 that selectively opens the cap 2 which seals the cylindrical aperture 1b of the reagent container 1, and a controller 19 that drives the cap opening device 20 to release the cylindrical aperture 1b from sealing by the cap 2 and that drops and inserts a probe 30 into the regent container 1.

The mounting table 11 is coupled to a shaft 16 that is rotatably supported by a bearing 15. The shaft 16 includes a gear 16a that engages with a gear 18a connected to a motor 18. The mounting table 11 is adapted to rotate for a predetermined amount by activating the motor 18 with a command from the controller 19 and by rotating the shaft 16 via the gears 18a and 16a.

The storage case 12 includes the cap opening device 20, a reagent house 13, and a lid 14 with an opening 14a for insertion of the probe 30. The cap opening device 20 is disposed inside the storage case 12.

The controller 19, when driving the opening device 20, receives a signal from a positioning sensor S that detects a position of a given reagent container 1 on the mounting table 11 and a signal from a reader R that read a reagent information on an information label attached to the flat portion 1c of the reagent container 1, and rotates the mounting table 11 to position the reagent container 1 to a dispensing position.

The cap opening device 20 includes an arm 21 that opens the cap 2 of the reagent containers 1, a slide shaft 22 that moves the arm 21 up and down, a rotary solenoid 24 that moves the slide shaft 22 up and down via a joint 23, and a guide 25 that guides the slide shaft 22. The arm 21 is provided with an opening 21a that is located immediately above the cap 2, and the opening 21a adjusts the position of the reagent container 1 relative to the arm 21 by engaging to a plurality of position control ribs 4e.

The automatic analyzer 10 configured in this way drives, under the control of the controller 19, the motor 18 to position a selected reagent container 1, which corresponds to a selected analysis, just below the probe 30, and drives the opening device 20 to make the arm 21 press the cap 2 of the reagent container 1 downward. At this time, since the cap 2 has, on the upper side of the top panel 4a, the plurality of position control ribs 4e that continuously become lower toward the outer circumference, the position of the reagent container 1 is adjusted to be in the same position relative to the arm 21 all time by making the plurality of position control ribs 4e and the opening 21a in engagement.

When the arm 21 pushes the cap 2 downward, in the reagent container 1, the slide member 4 of the cap 2 is pressed down, accordingly, the flap member 4h is raised along with the sealing member 5 which is sealing the upper opening 3f of the insertion cylinder 3c, and the upper opening 3f is opened. Then, the probe 30 is descended and inserted into the reagent container 1 through the upper opening 3f of the insertion cylinder 3c by a driving device (not shown in Figures) to suck the reagent. The automatic analyzer 10 stops driving of the opening device 20 and releases the cap 2 from pressure of the arm 21 after sucking the reagent, then, the biasing member 6 pushes up the slide member 4 with its pressuring force by the reverse method. Thus, in the reagent container 1, the slide member 4 returns to the initial position, the flap member 4h is laid down, and the upper opening 3f of the insertion cylinder 3c is closed by the sealing member 5.

Figure 25:
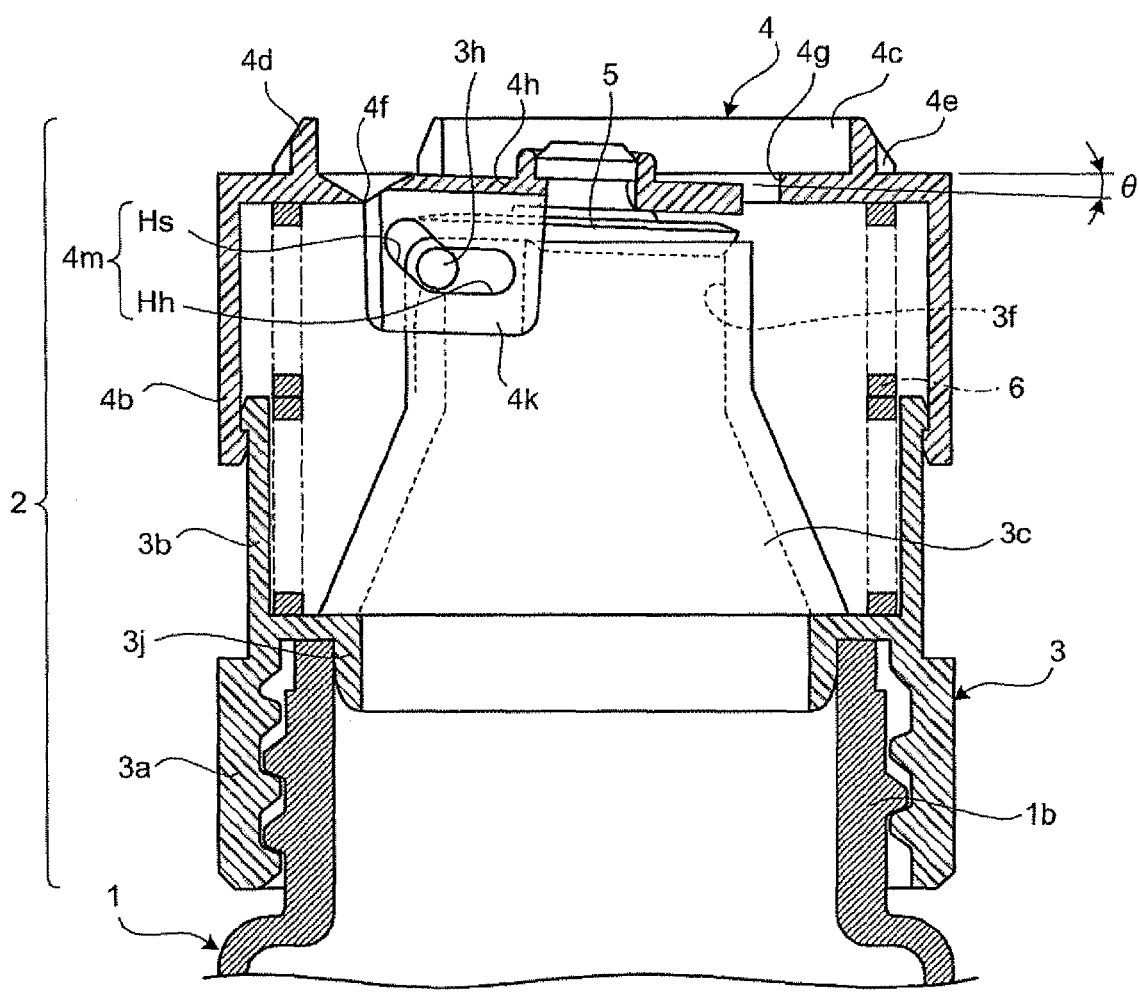
FIG. 25 is an enlarged view of the upper part of the reagent container in FIG. 1 with the sealing member sealing an opening of an insertion cylinder.

The motion of the cap 2 during opening and closing will be described below with reference to FIGS. 25 to 31. First, as in the cap 2 shown in FIG. 25 that is an enlarged illustration of the upper part of FIG. 1, the slide member 4 is normally pressed upward by the pressing force of biasing member 6, and the upper opening 3f is closed with the sealing member 5 that has almost the same diameter as the upper opening 3f. At this time, in the cap 2, the protrusion 3h that is formed on the upper part of the insertion cylinder 3c as a fixed point engages with the long hole Hh that extends along the guiding hole 4m formed in the guiding piece 4k. Thus, in the flap member 4h, the guiding piece 4k that is engaging with the engaging protrusion 3h by the pressing force of the biasing member 6 is pushed downward, and, as shown in FIG. 25, the opposite side to the hinge 4f is declined at a slight angle around the hinge 4. In this condition, the seal convex 5i (see FIG. 16) on the outer circumference in the lower part tightly fits to the sealing portion 3n (see FIG. 8) without clearance to cause the sealing member 5 to seal the upper opening 3f.

Figure 26:
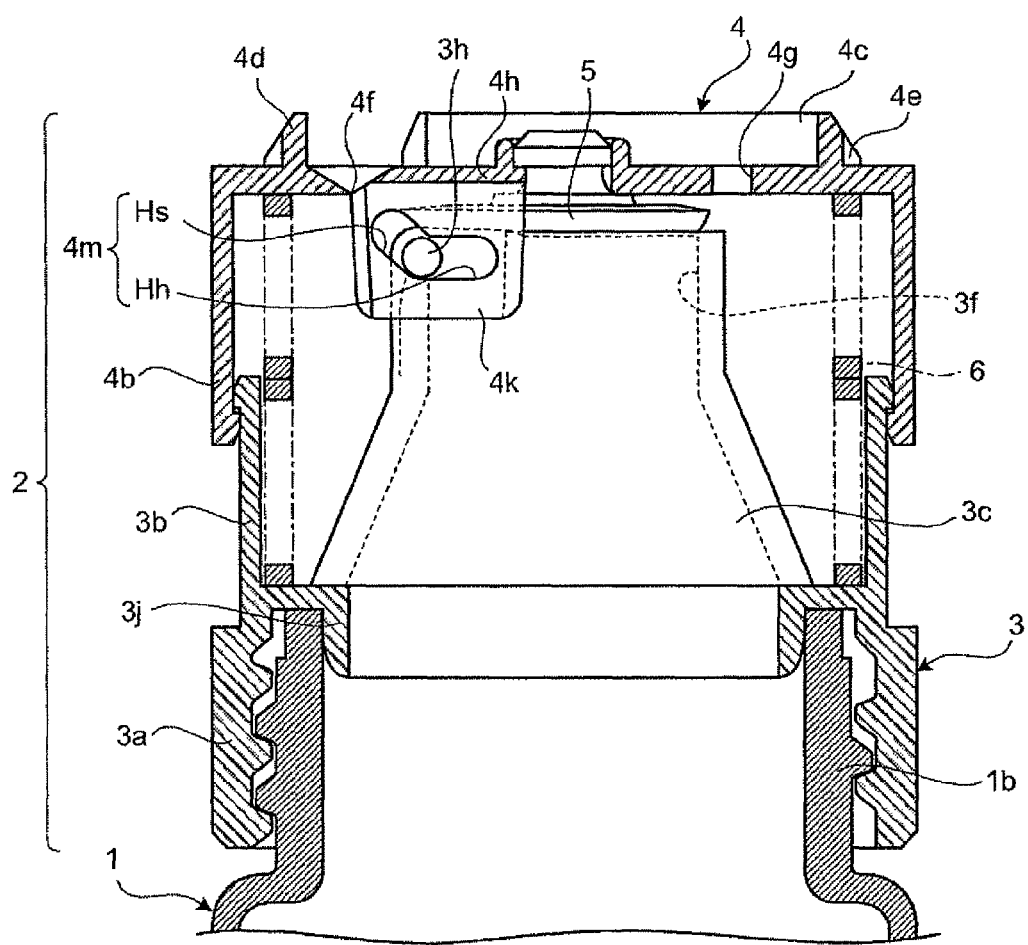
FIG. 26 is an enlarged view of the flap member and the sealing member in a virtual horizontal position where the slide member of the cap of FIG. 25 is slightly pressed down.

Then, the slide member 4 of the cap 2 is slightly pushed down by the arm 21 that is droved by the opening and closing device 20, and the guiding pieces 4k are slightly pushed up by the engaging protrusion 3h, so as shown FIG. 26, the flap member 4h slightly rotates in counterclockwise direction around the hinge 4f to be almost horizontalized. However, although the flap member 4h is horizontalized, the seal convex 5i (see FIG. 16) on the outer circumference in the lower part tightly fits to the sealing portion 3n (see FIG. 8) without clearance to cause the sealing member 5 to seal the upper opening 3f. At this time, as shown in FIG. 26, the engaging protrusion 3h is located at the boundary of the long hole Hh that extends in horizontal direction of the guiding hole 4m and the long hole Hs that is slanted relative to the horizontal direction.

Figure 27:
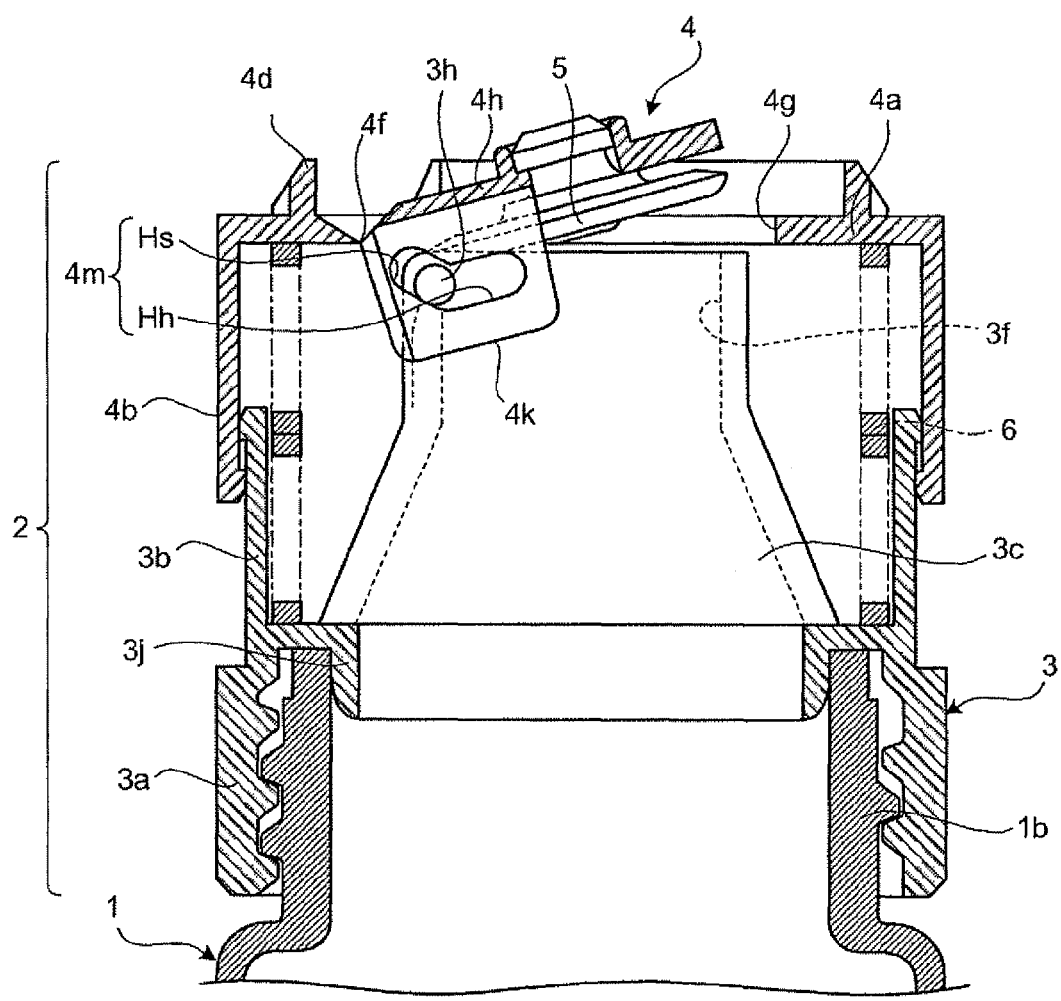
FIG. 27 is an enlarged view of the flap member and the sealing member in an inclined position where the flap member is raised with the slide member further pressed down and the sealing member releases the sealing of the opening of the insertion cylinder.

After that, when the slide member 4 of the cap 2 is further pressed down, since the engaging protrusion 3h is the fixed point, the long hole Hs of the guiding piece 4m gradually moves toward the engaging protrusion 3h side. The engaging protrusion 3h apparently moves left in the long hole Hs, and the flap member 4h further rotates in counterclockwise direction around the hinge 4f to start to rise. As a result, as shown in FIG. 27, the reagent container 1 is released from sealing of the upper opening 3f by the sealing member 5, and the flap member 4h along with the sealing member 5 is placed inclined around the hinge 4f.

At this time, the sealing member 5 starts to rise along with the flap member 4h. The sealing portion 5g has a diameter between an inner diameter of the upper opening 3f and an outer diameter of the upper part of the insertion cylinder 3c, and the flange 5, with its bottom side, contacts with the upper circumference of the upper opening 3f and the two ribs 3k provided on the outer circumference of the upper part of the insertion cylinder 3c. Thus, the sealing member 5 smoothly closes or opens without dropping the sealing portion 5g into the upper opening 3f. Also, as shown in FIG. 13, since the upper surface of the sealing portion 5g adjacent to the lower locking part 5c is pressed by the protrusions P provided at two sections on the bottom surface of the flap member 4h, deflection on the flange 5j side is suppressed. Furthermore, because of the presence of the concave 4p, when the sealing member 5 is raised and laid, the slanted portion 5 of the sealing member 5 is regulated to avoid a contact with the bottom surface of the flap member 4h. Then, the movement of the long hole Hs of the guiding hole 4m toward the engaging protrusion 3h side by pressing down the sliding member 4, as shown in FIG. 28, continues until the long hole Hs is horizontalized, and the flap member 4h rotates in counterclockwise direction around the hinge 4f to rise at about 45°.

Figure 28:
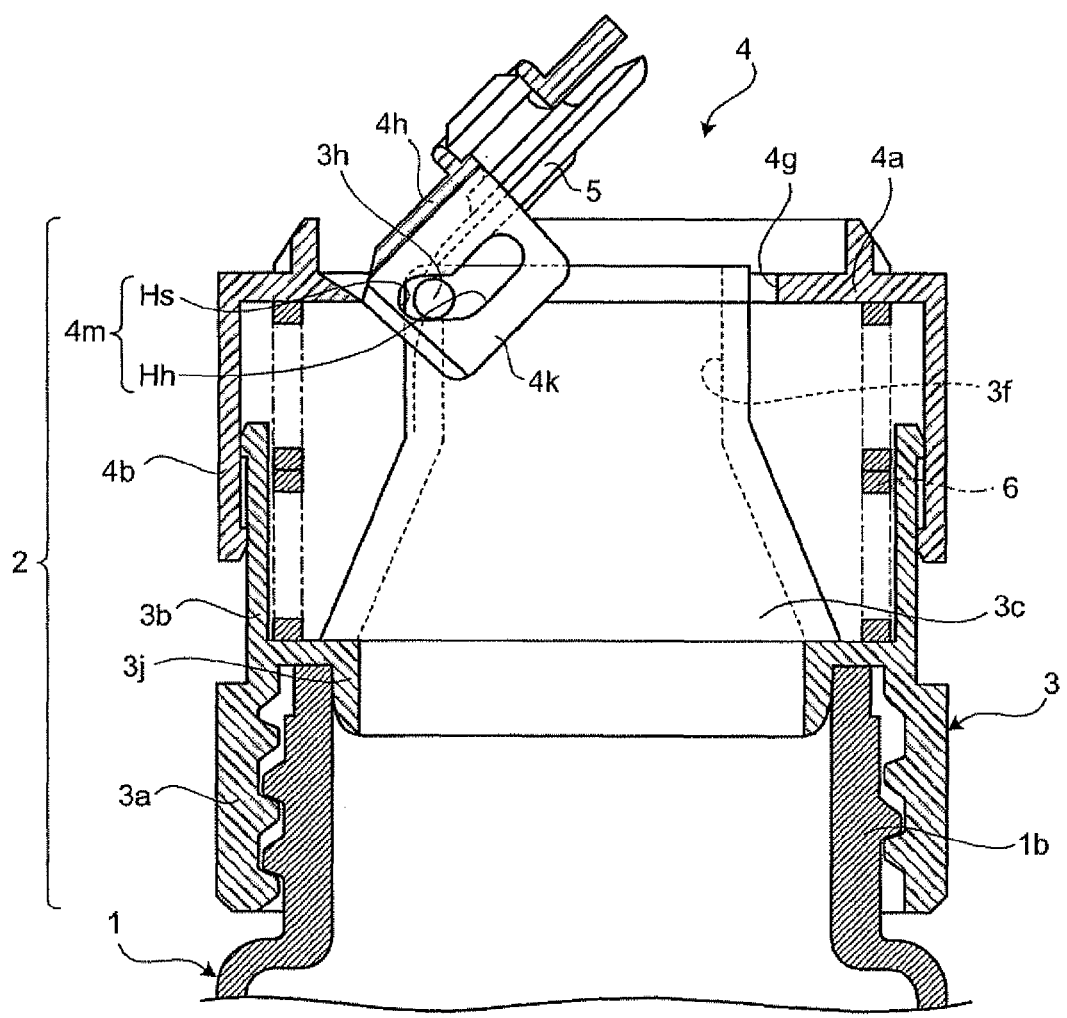
FIG. 28 is an enlarged view showing that the flap member and the sealing member are raised by about 45° with the slide member further pressed down.
Figure 29:
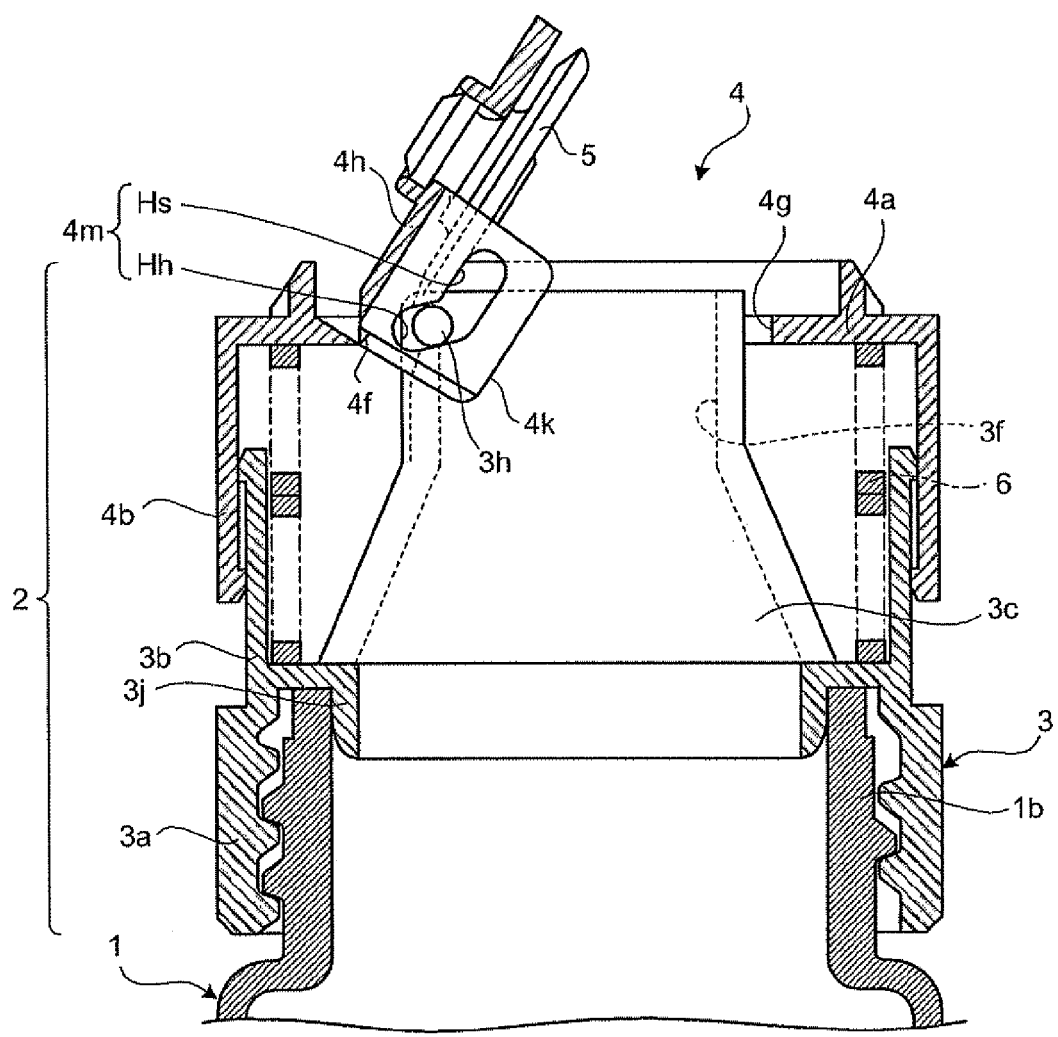
FIG. 29 is an enlarged view showing the condition where the slide member is further pressed down after the condition indicated in FIG. 28.

When the slide member 4 of the cap 2 is further pushed down from the position shown in FIG. 28, the guiding piece 4k is pressed up by the protrusions 3h, and the flap member 4h rotates in counterclockwise direction around the hinge 4f to further rise as shown in FIG. 29.

Figure 30:
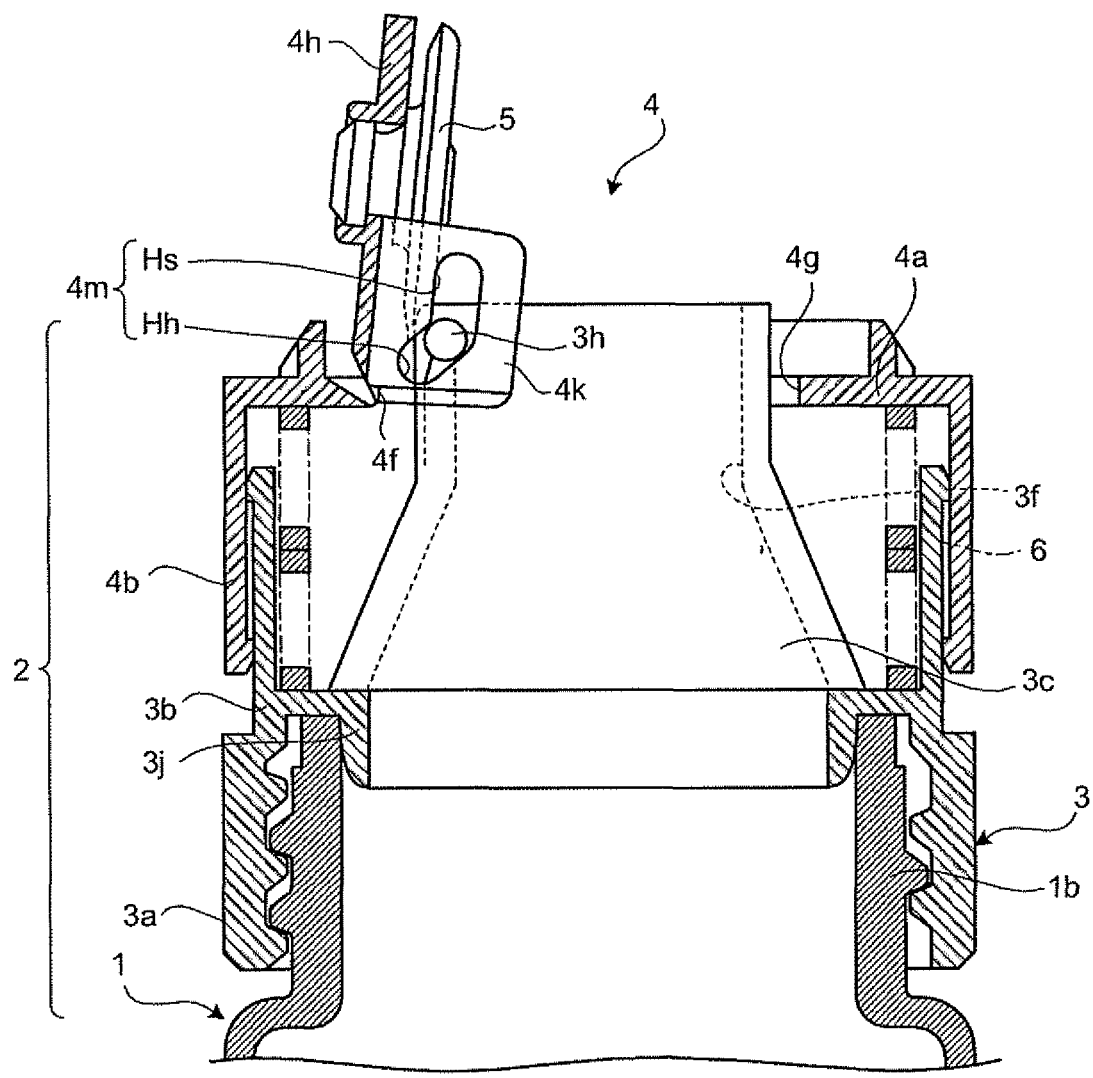
FIG. 30 is an enlarged view showing the condition where the slide member is further pressed down after the condition shown in FIG. 29.

When the slide member 4 of the cap 2 is further pushed down from the position shown in FIG. 29, as shown in FIG. 30, the long hole Hs of the guiding hole 4m moves downward, the engaging protrusion 3h apparently moves toward the long hole Hh from the long hole Hs, and the flap member 4h further rotates in counterclockwise direction around the hinge 4f to rise.

Figure 31:
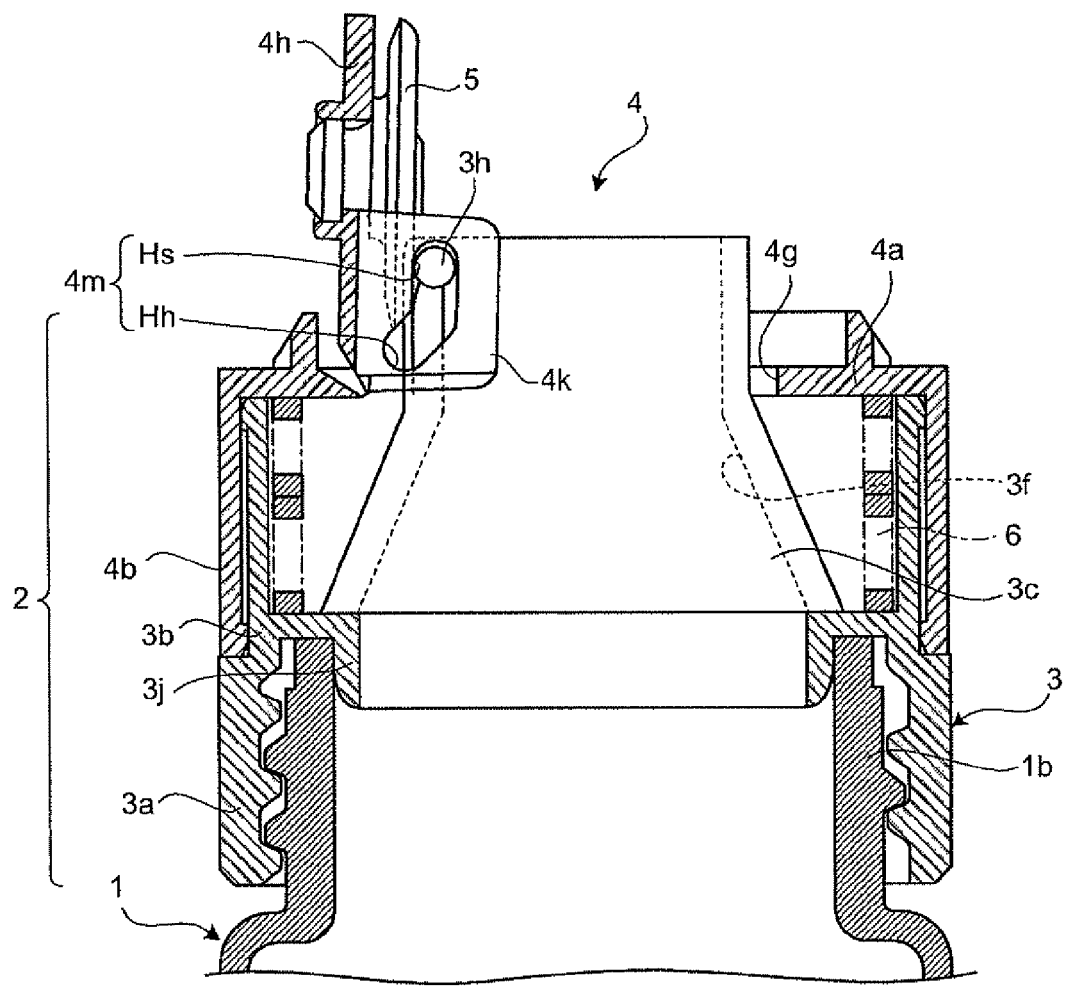
FIG. 31 is an enlarged view showing that the slide member is pressed down to the end, that the flap member and the sealing member are raised to upright, and that the opening of the insertion cylinder is fully opened.

When the slide member 4 is pushed down to the end, as shown in FIG. 31, the engaging protrusion 3h apparently moves to the end of the long hole Hh, and the flap member 4h rotates around the hinge 4f and rises at 90° relative to the horizontal plane. The reagent container 1 is fully opened in that the upper opening 3f of the insertion cylinder 3c is opened. Therefore, in this condition of the reagent container it the inside reagent is sucked by the probe 30 that is inserted from the upper opening 3f.

After the reagent in the reagent container 1 is sucked, the pressuring force by the arm 21 is released, the slide member 4 is pushed up by the pressing force of the biasing member 6 to lay down the flap member 4h in the opposite way described above, and the upper opening 3f is again sealed by the sealing member 5. When the flap member 4h is laid down, in the same way as the flap member 4h is raised, the sealing member 5 smoothly closes and opens without dropping the sealing portion 5g into the upper opening 3f. Here, because the flap member 4h is linked with the top panel 4a by the thin-walled hinge 4f, the rising and laying action is smoothly carried out. Meanwhile, the reagent sucked by the probe 30 is discharged into a reaction container containing dispensed analyte, not shown in figures, and a reactant after a reaction of the reagent and the analyte is analyzed. The automatic analyzer 10 continuously carries out analysis for several kinds of item analysis by repeating these actions.

As described above, the sealing member 5 contacts with the upper edge of the upper opening 3f, and the flange 5j is provided to the outer circumference of the sealing portion 5g on the hinge 4f side as an extending part that extends outward of the upper opening 3f. Therefore, when raised and laid down along with the flap member 4h, the sealing member 5 is regulated that the sealing portion 5g does not fall into the upper opening 3f by making the flange 5; contacts with the upper edge of the upper opening 3f. Therefore, when the sealing member 5 is raised or laid down along with the flap member 4h to open or close the upper opening 3f, the flange 5j rises or lies, contacting with the upper edge of the upper opening 3f and the upper surface of two ribs 3k arranged on the outer circumference of the upper part of the insertion cylinder 3c, so the sealing member 5 is smoothly opens and closes without dropping the sealing portion 5g into the upper opening 3f. At this time, since the sealing member 5 is provided with the positioning rib 5f, by fitting the positioning rib 5f into the concave 43 to attach the holding portion 5a in the insertion hole 4i, the sealing member 5 can position the flange 5j in the hinge 4f side without taking a wrong attaching direction. Also, the cap 2 with the sealing member 5 has a simple structure as compared with a conventional cap disclosed in Japanese patent application laid-open No. 2004-177255, and costs less to manufacture because of a fewer number of parts.

On the other hand, regarding to the reagent container 1, the slide member 4 is normally pressed upward by the pressing force of biasing member 6 to seal the upper opening 3*f* with the sealing member 5, and the upper opening 3*f* is opened only if the slide member 4 is pushed down when dispensing, etc. In addition, the sealing portion 5*g* is shaped in a discoid, is formed to become lower outward on the circumference of its upper part, and does not have a slit. Thus, the reagent container 1 prevents the reagent from vaporization, and if a liquid such as condensed water in the reagent storage 13 and a reagent in another reagent container 1 flies apart, the reagent container 1 prevents a liquid entering from a clearance between the opening 4*g* of the top panel 4*a* and the flap member 4*h*.

Also, even though a liquid such as condensed water enters the cap 2 from the clearance between the opening 4*g* and the flap member 4*h*, because the cap 2 has a slanted portion 5*k* that becomes lower outward on the outer circumference of the upper part of the sealing portion 5*g*, the entering condensed water flows down the upper surface of the sealing portion 5*g* to outward and is discharged outside of the insertion cylinder 3*c* in radial direction. Therefore, an occurrence of a contamination that is caused by entering a liquid such as condensed water in the reagent storage 13 and a reagent flied apart from another reagent container 1 is avoided. Furthermore, since the cap 2 has a simple structure and fewer parts as compared with a conventional cap, the cap 2 is supplied at a lower cost, thus the reagent container 1 is supplied at a lower cost.

Here, for the retainer 3, the attachment portion 3*a* is applied, on its outer surface, with the knurling 3*d*, so that the attachment portion 3*a* is easily screwed into the cylindrical aperture 1*b* by holding the knurling portion 3*d* with fingertips and rotating the retainer 3. At this time, the cap 2 is already assembled by attaching the slide member 4 to the retainer 3, the slide member 4 may come away from the retainer 3 because the slide member 4 may also rotate in circumferential direction when the retainer 3 is rotated.

Figure 32:
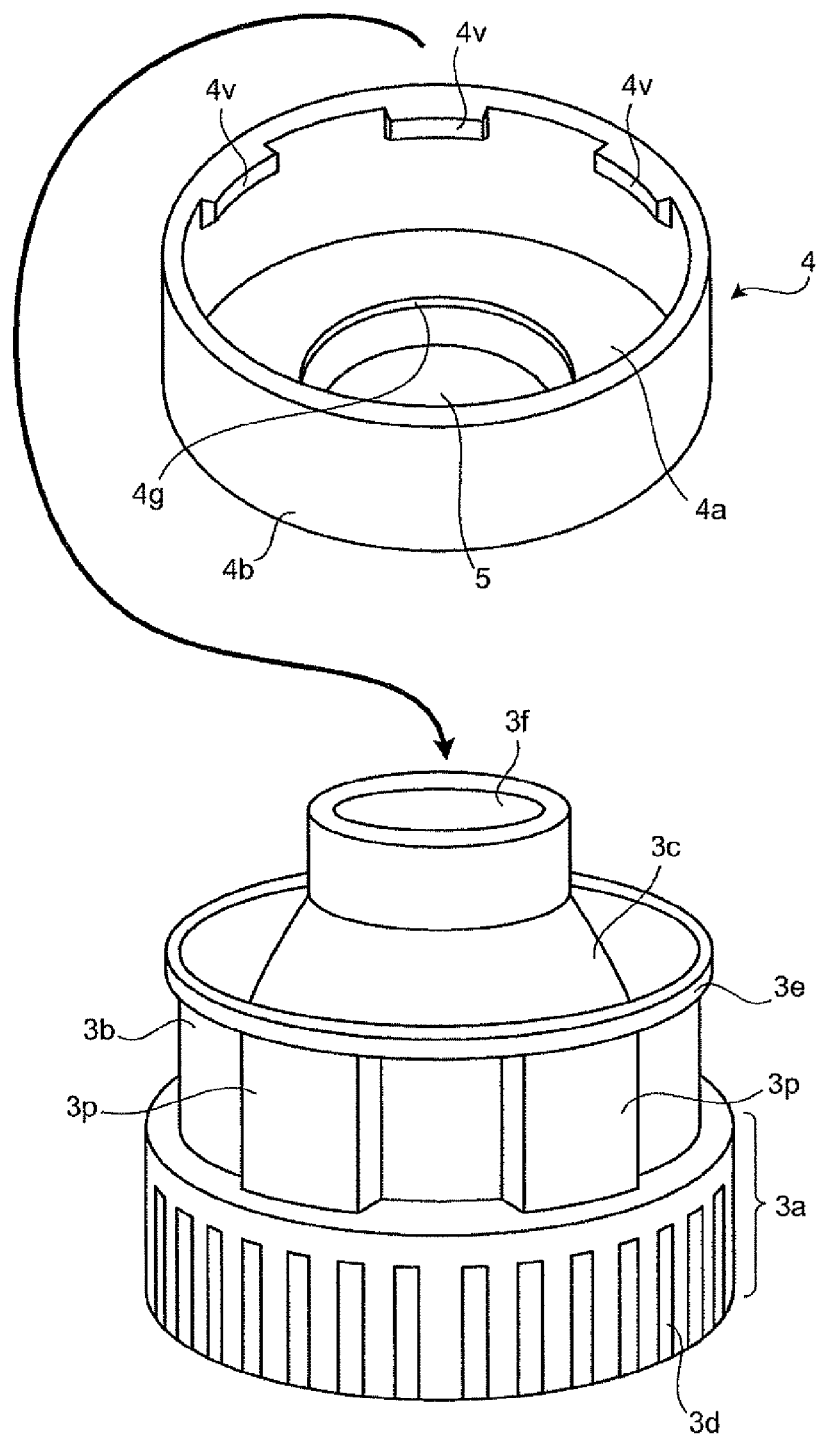
FIG. 32 is a perspective view showing a modification of the retainer and the slide member constituting the cap.

For this reason, as shown in FIG. 32, the cap 2 includes, at the bottom part of the engaging portion 3*e* on the outer surface of the guiding cylinder 3*b* of the retainer 3, two stoppers 3*p* that is place at a distance apart in the circumferential direction on above and below. On the other hand, the slide member 4 is provided, at a position adjacent to the two stoppers 3*p*, with three protrusions 4*v* that engage with the engaging portion 3*e* as shown in FIG. 32. At this time, the three protrusions 4*v* are arranged in such a way that the middle protrusion 4*v* is placed between the two stoppers 3*p*, and the other two protrusions are arranged outside of the stoppers 3*p*. Therefore, the slide member 4 is vertically turned over and attached to the retainer 3 as indicated by the arrow to make the protrusions 4*v* and the stopper 3*p* in engagement. Then, the protrusions 4*u*, 4*v* and the engaging portion 3*e* regulate the slide member 4 not to fail off from the retainer 3 even if the slide member 4 slides with respect to the retainer 3, and regulate the slide member 4 not to rotate in the circumferential direction with respect to the retainer 3 by placing the protrusions 4*v* and the stoppers 3*p* in engagement. These prevent the slide member 4 from falling off from the retainer 3.

The sealing member of the embodiment of the present invention has, on the outer circumference in the predetermined side of the sealing portion, an extending portion that extends outward of the opening of the cap. Since the extending portion contacts with the upper edge of the opening when the sealing portion covers the opening, the extending portion restricts the sealing member not to fall into the opening. Thus, the sealing member of the present invention smoothly opens and closes, and the cap for the reagent container with the sealing member according to the present invention has a simple structure with a fewer parts.

The reagent container of the embodiment of the present invention has the sealing member that is supported by the flap member of the slide member to close the opening of the insertion cylinder possessed by the retainer, and that slides the slide member toward the retainer side to open the opening of the insertion cylinder by raising along with the flap member. Thus, when used with the automatic analyzer, the reagent container of the present invention is effective to reduce occurrence of a contamination even if liquid such as condensed water in the reagent storage of the automatic analyzer and reagent from another reagent container spatters, because such liquid is difficult to enter the container.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A sealing member comprising a sealing portion that is used for a cap attached to a reagent container and covers an opening of the cap with an open-close movement by flapping around a predetermined point, wherein
   the sealing portion has, on an outer circumference in the predetermined point side, an extending portion that extends outward of the opening, and
   the extending portion contacts with an upper edge of the opening while the sealing portion is raised to open the opening and laid down to close laid down to close the opening.

2. The sealing member according to claim 1, further comprising, at a position adjacent to the sealing portion, a positioning portion that positions the extending portion in the predetermined point side.

3. A cap for a reagent container, attached to a cylindrical opening of a main body containing a reagent, the cap comprising:
   a retainer that has an insertion cylinder connected to the cylindrical opening and that is attached to the cylindrical opening;
   a slide member that slidably fits in the retainer to cover the retainer and that has a flap member being raised and laid by the insertion cylinder according to a sliding motion against the retainer;
   a sealing member that is supported by the flap member and that seals an opening of the insertion cylinder with an open-close movement; and
   a biasing member that is placed between the retainer and the slide member to press the slide member toward the opposite direction from the retainer and that gives a pressing force to make the sealing member seal the opening of the insertion cylinder via the slide member, wherein
   the sealing member includes a sealing portion that has, on an outer circumference in a predetermined point side, an extending portion that extends outward of the opening, and the extending portion contacts with an upper edge of the opening while the sealing portion is raised to open the opening and laid down to close laid down to close the opening.

4. A reagent container comprising a cap attached to a cylindrical opening of a main body containing a reagent, wherein the cap includes
 a retainer that has an insertion cylinder connected to the cylindrical opening and that is attached to the cylindrical opening;
 a slide member that slidably fits in the retainer to cover the retainer and that has a flap member being raised and laid by the insertion cylinder according to a sliding motion against the retainer;
 a sealing member that is supported by the flap member and that seals an opening of the insertion cylinder; and
 a biasing member that is placed between the retainer and the slide member to press the slide member toward the opposite direction from the retainer and that gives a pressing force to make the sealing member seal the opening of the insertion cylinder via the slide member, and
 wherein the sealing member is raised up along with the flap member by the insertion cylinder by sliding the slide member toward the retainer to open the opening, and
 the sealing member includes a sealing portion that has, on an outer circumference in a predetermined point side, an extending portion that extends outward of the opening, and the extending portion contacts with an upper edge of the opening while the sealing portion is raised to open the opening and laid down to close laid down to close the opening.

5. The reagent container according to claim 4, wherein the insertion cylinder includes engaging protrusions at facing positions on an outer circumference of an upper part across a center of the cylinder, and the flap member includes a guiding portion that guides the raising and laying motion of the flap member by engaging each engaging protrusion to a corresponding facing position.

6. The reagent container according to claim 4, wherein the slide member includes, on an upper side, an adjusting portion adjusting the position of an operating means that slides the slide member toward the retainer.

7. The reagent container according to claim 5, wherein the slide member includes, on an upper side, an adjusting portion adjusting the position of an operating means that slides the slide member toward the retainer.

8. The reagent container according to claim 4, wherein the flap member includes a positioning portion that determines a position at which the sealing member is supported.

9. The reagent container according to claim 5, wherein the flap member includes a positioning portion that determines a position at which the sealing member is supported.

10. The reagent container according to claim 6, wherein the flap member includes a positioning portion that determines a position at which the sealing member is supported.

11. The reagent container according to claim 4, wherein the flap member is formed in thin-walled, and has a hinge as a pivotal point of the raising and laying motion.

12. The reagent container according to claim 5, wherein the flap member is formed in thin-walled, and has a hinge as a pivotal point of the raising and laying motion.

13. The reagent container according to claim 6, wherein the flap member is formed in thin-walled, and has a hinge as a pivotal point of the raising and laying motion.

14. The reagent container according to claim 8, wherein the flap member is formed in thin-walled, and has a hinge as a pivotal point of the raising and laying motion.

15. The reagent container according to claim 4, wherein the insertion cylinder includes a plurality of contact portions that contact with a circumference of a bottom part of the hinge side of the sealing member, and that are formed on an outer circumference of an upper part.

16. The reagent container according to claim 4, wherein the sliding member includes a regulation portion that regulates a movement toward an opposite direction from the retainer by engaging an engaging portion of the retainer with an engaging portion of the retainer.

17. The reagent container according to claim 5, wherein the guiding portion includes a slanted ditch that guides the engaging protrusions.

18. The reagent container according to claim 17, wherein the facing guiding portions are placed on a top panel, and a concave that regulates a contact of the sealing member is arranged between the guiding portions on the bottom side of the top panel.

19. The reagent container according to claim 4, wherein the retainer includes a plurality of stoppers that are arranged along a sliding direction of the slide member, and the slide member includes a plurality of regulating protrusions that regulate a rotation in a circumferential direction by engaging with the plurality of stoppers.

* * * * *

UNITED STATES PATENT AND TRADEMARK OFFICE
CERTIFICATE OF CORRECTION

PATENT NO.           : 8,613,893 B2
APPLICATION NO.      : 12/029257
DATED                : December 24, 2013
INVENTOR(S)          : Naoki Ohashi et al.

Page 1 of 1

It is certified that error appears in the above-identified patent and that said Letters Patent is hereby corrected as shown below:

In the Claims

In Column 12, line 36-37 please replace "opening and laid down to close laid down to close the opening." with -- opening and laid down to close the opening. --

In Column 12, line 66-67 please replace "the opening and laid down to close laid down to close the opening." with -- the opening and laid down to close the opening. --

In Column 13, line 27-28 please replace "the opening and laid down to close laid down to close the opening." with -- the opening and laid down to close the opening. --

Signed and Sealed this
Twenty-ninth Day of April, 2014

Michelle K. Lee
*Deputy Director of the United States Patent and Trademark Office*